US010786172B2

(12) United States Patent
Perschbacher et al.

(10) Patent No.: US 10,786,172 B2
(45) Date of Patent: Sep. 29, 2020

(54) SYSTEMS AND METHODS FOR ATRIAL ARRHYTHMIA DETECTION

(71) Applicant: Cardiac Pacemakers, Inc., St. Paul, MN (US)

(72) Inventors: David L. Perschbacher, Coon Rapids, MN (US); Sunipa Saha, Shoreview, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 189 days.

(21) Appl. No.: 15/914,582

(22) Filed: Mar. 7, 2018

(65) Prior Publication Data

US 2018/0256059 A1 Sep. 13, 2018

Related U.S. Application Data

(60) Provisional application No. 62/468,165, filed on Mar. 7, 2017.

(51) Int. Cl.
*A61B 5/04* (2006.01)
*A61B 5/0464* (2006.01)
(Continued)

(52) U.S. Cl.
CPC ............ *A61B 5/0464* (2013.01); *A61B 5/024* (2013.01); *A61B 5/02405* (2013.01);
(Continued)

(58) Field of Classification Search
CPC ... A61B 5/0464; A61B 5/4836; A61B 5/7264; A61B 5/024; A61B 5/02405;
(Continued)

(56) References Cited

U.S. PATENT DOCUMENTS 6,490,479 B2 12/2002 Bock
6,922,584 B2 7/2005 Wang et al.
(Continued)

FOREIGN PATENT DOCUMENTS

| CN | 110573068 A | 12/2019 |
|----|-------------|---------|
| JP | 2020511216 A | 4/2020 |
| WO | WO-2018165289 A1 | 9/2018 |

OTHER PUBLICATIONS

Sanna, Tommaso, et al., "Cryptogenic Stroke and Underlying Atrial Fibrillation", N Engl J Med 2014;370:2478-86.
"European Application Serial No. 18712388.0, Response to Communication Pursuant to Rules 161(1) and 162 EPC filed Apr. 9, 2020", 19 pgs.
"International Application Serial No. PCT/US2018/021330, International Preliminary Report on Patentability dated Sep. 19, 2019", 8 pgs.

(Continued)

*Primary Examiner* — Mallika D Fairchild
(74) *Attorney, Agent, or Firm* — Schwegman Lundberg & Woessner, P.A.

(57) ABSTRACT

Systems and methods for detecting atrial arrhythmias such as atrial tachyarrhythmia (AT) are described herein. An AT detection system may include a heart rate detector circuit configured to detect, from a physiological signal, representative ventricular heart rates within heart rate analysis windows. An atrial tachyarrhythmia detector circuit may perform an initial rate detection using a first ventricular heart rate statistic generated from the representative ventricular heart rates, and to perform a sustained arrhythmia detection using one or more second ventricular heart rate statistics generated within a second plurality of heart rate analysis windows during a specific duration. An AT event is detected if the second ventricular heart rate statistics satisfy a specific condition throughout the specific duration. The AT detection system may include an output unit that may output the detected AT to a user or a process.

20 Claims, 6 Drawing Sheets

(51) Int. Cl.
*A61B 5/00* (2006.01)
*A61B 5/024* (2006.01)
*A61N 1/365* (2006.01)
*A61N 1/362* (2006.01)

(52) U.S. Cl.
CPC .......... *A61B 5/4836* (2013.01); *A61B 5/7232* (2013.01); *A61B 5/7264* (2013.01); *A61B 5/7271* (2013.01); *A61N 1/362* (2013.01); *A61N 1/36592* (2013.01); *A61B 2562/0247* (2013.01)

(58) Field of Classification Search
CPC ................ A61B 5/7232; A61B 5/7271; A61B 2562/0247; A61N 1/362; A61N 1/36592
See application file for complete search history.

(56) References Cited

U.S. PATENT DOCUMENTS

2015/0250428 A1 9/2015 Zhang et al.
2015/0342466 A1* 12/2015 Thakur .............. A61N 1/36585
  600/484
2017/0281034 A1* 10/2017 Higgins ............... A61B 5/0006

OTHER PUBLICATIONS

"International Application Serial No. PCT/US2018/021330, International Search Report dated May 16, 2018".
"International Application Serial No. PCT/US2018/021330, Written Opinion dated May 16, 2018".

* cited by examiner

SYSTEMS AND METHODS FOR ATRIAL ARRHYTHMIA DETECTION

CLAIM OF PRIORITY

This application claims the benefit of priority under 35 U.S.C. § 119(e) of U.S. Provisional Patent Application Ser. No. 62/468,165, filed on Mar. 7, 2017, which is herein incorporated by reference in its entirety.

TECHNICAL FIELD

This document relates generally to medical devices, and more particularly, to systems, devices and methods for detecting and managing cardiac arrhythmias.

BACKGROUND

Implantable medical devices (IMDs) have been used for monitoring patient health condition or disease states and delivering therapies. For example, implantable cardioverter-defibrillators (ICDs) may be used to monitor for certain abnormal heart rhythms and to deliver electrical energy to the heart to correct the abnormal rhythms. Some IMDs may be used to monitor for chronic worsening of cardiac hemodynamic performance, such as due to congestive heart failure (CHF), and to provide cardiac stimulation therapies, including cardiac resynchronization therapy (CRT) to correct cardiac dyssynchrony within a ventricle or between ventricles.

Some IMDs are capable of detecting cardiac arrhythmias, such as atrial tachyarrhythmia (AT). One type of AT is atrial fibrillation (AF), recognized as the most common clinical arrhythmia affecting millions of people. During AF, disorganized electrical pulses originated from regions in or near an atrium may lead to irregular conductions to ventricles, thereby causing inappropriately fast and irregular heart rate. AF may be paroxysmal that may last from minutes to days before it stops by itself, persistent that may last for over a week and typically requires medication or other treatment to revert to normal sinus rhythm, or permanent where a normal heart rhythm cannot be restored with treatment.

Another type of AT is atrial flutter (AFL). AFL usually accompanies with some degree of atrioventricular (AV) node conduction block, and can be associated with a fast and usually regular heart rate. Typical or Type I AFL may involve a single reentrant circuit in the right atrium around the tricuspid valve annulus, and has an atrial rate of 240 to 340 beats per minute (bpm). The reentrant circuit most often travels in a counter-clockwise direction. Atypical or Type II AFL follows a different circuit, which may involve the right or the left atrium, and usually has a faster atrial rate of around 340-440 bpm. AFL may be associated with a variety of cardiac disorders, such as coronary artery disease (CAD) or hypertensive heart disease. AFL may often degenerate into AF. Prolonged fast AFL may lead to decompensation with loss of normal heart function. This may manifest as effort intolerance, nocturnal breathlessness, or swelling of the legs or abdomen. Timely detection of AT, such as AF or AFL, may be clinically important for assessing cardiac function.

Overview

Some IMDs are capable of detecting physiological events, such as cardiac arrhythmias or progression of chronic heart diseases, and obtaining sampled values of cardiac electrical activity signals such as electrograms. Some IMDs may further be communicated with multiple physiological sensors that may measure various physiological signals. Capturing accurate electrogram or other physiological sensor information obtained over a longer period of time, such as chronically between regularly-scheduled outpatient office visits, may help the physician re-program the device, if needed, diagnose cardiac disease, or assess the patient's health status.

Atrial tachyarrhythmias such as AF or AFL are characterized by fast atrial rate. In some patients, direct sensing of atrial activation rate with an electrode positioned in the atrium is not available or not feasible, such as patients not indicated for atrial lead implantation. A medical device, such as a single-chamber IMD with no dedicated atrial sensing/pacing lead, may detect the AT based on heart rate, and not on direct sensing of atrial activity from the atrium. However, confounding factors such as noise, motion artifacts, or cardiac rhythms other than the AT may be mistakenly detected as AT events. For example, during AFL, impulses from the atria are conducted to the ventricles through the atrio-ventricular node (AV node). Due primarily to its longer refractory period, the AV node may exert a protective effect on heart rate at the ventricle by blocking atrial impulses in excess of approximately 180 beats per minute (bpm). If an AFL rate is 300 bpm, a two-to-one (2:1) heart block may develop such that only half of the atrial impulses can be conducted to the ventricle, resulting in a ventricular rate of 150 bpm. As the heart rate is a measure of the ventricular rather than atrial activity, a medical device that detects AT based on ventricular heart rate and not on atrial activity may be confounded by physiological sinus rhythm at an elevated rate such as during tolerable physical activities (e.g., sinus tachycardia). The inappropriate detections may decrease detection specificity, and result in unnecessary or inappropriate medical or device therapies. False alerts to clinicians of the inappropriately detected arrhythmia, or presenting to clinicians a large volume of inappropriately detected arrhythmic events for review or adjudication, may adversely affect the device efficacy and unwarrantedly increase the healthcare cost associated with patient management. Consequently, this may diminish the clinical utility of the heart rate-based AT detection. For at least these reasons, the present inventors have recognized, among other things, substantial challenges and a demand for a more efficient system and methods for AT detection.

This document discusses, among other things, systems, devices, and methods for detecting atrial tachyarrhythmias. An AT detection system may include a sensor circuit to sense a physiological signal, and a heart rate detector circuit to detect representative ventricular heart rates within heart rate analysis windows. An atrial tachyarrhythmia detector circuit may perform an initial rate detection using a first ventricular heart rate statistic generated from the representative ventricular heart rates within a first plurality of heart rate analysis windows, and to perform a sustained arrhythmia detection using one or more second ventricular heart rate statistics generated from a plurality of representative ventricular heart rates determined within a second plurality of heart rate analysis windows during a specific duration. An AT event is detected if the second ventricular heart rate statistics satisfy a specific condition throughout the specific duration. The AT detection system may include an output unit that may output the detected AT to a user or a process.

Example 1 is a system for detecting atrial arrhythmias. The system comprises an atrial tachyarrhythmia detector circuit that may generate a first ventricular heart rate statistic using a plurality of representative ventricular heart rates determined within a first plurality of heart rate analysis windows, and generate one or more second ventricular heart rate statistics during a specific duration, where the one or more second ventricular heart rate statistics each may be generated from a plurality of representative ventricular heart rates determined within a second plurality of heart rate analysis windows. The atrial tachyarrhythmia detector circuit may detect an atrial tachyarrhythmia (AT) event in response to the first ventricular heart rate statistic satisfying a first condition and the one or more second ventricular heart rate statistics satisfying a second condition throughout the specific duration.

In Example 2, the subject matter of Example 1 optionally includes a therapy circuit configured to generate and deliver a cardiac therapy or a neural therapy in response to the detection of the AT.

In Example 3, the subject matter of any one or more of Examples 1-2 optionally includes detecting the AT event including an atrial flutter event or an atrial fibrillation event.

In Example 4, the subject matter of any one or more of Examples 1-3 optionally includes the plurality of representative ventricular heart rates, each of which may include a central tendency indicating a most frequent heart rate among ventricular heart rate measurements within a respective heart rate analysis window.

In Example 5, the subject matter of any one or more of Examples 1-4 optionally includes the first ventricular heart rate statistic that may include a first relative number of the representative ventricular heart rates, within the first plurality of heart rate analysis windows, that exceed a heart rate threshold.

In Example 6, the subject matter of Example 5 optionally includes the atrial tachyarrhythmia detector circuit that may be configured to generate one or more second ventricular heart rate statistics in response to the first ventricular heart rate statistic satisfying the first condition indicating that at least eight out of ten representative ventricular heart rates, determined from ten consecutive heart rate analysis windows, exceed the heart rate threshold.

In Example 7, the subject matter of any one or more of Examples 1-6 optionally includes the one or more second ventricular heart rate statistics that may include second relative number of the representative ventricular heart rates, within the second plurality of heart rate analysis windows, that exceed a heart rate threshold.

In Example 8, the subject matter of Example 7 optionally includes the atrial tachyarrhythmia detector circuit that may be configured to detect the AT event in response to the one or more second ventricular heart rate statistics satisfying the second condition indicating that at least six out of ten representative ventricular heart rates, determined from any ten consecutive heart rate analysis windows throughout the specific duration, exceed the heart rate threshold.

In Example 9, the subject matter of any one or more of Examples 7-8 optionally includes the AT event that may include an atrial flutter event, and the heart rate threshold is programmable between 100 and 150 beats per minute.

In Example 10, the subject matter of any one or more of Examples 7-9 optionally includes detecting the AT event including an atrial flutter event, and the specific duration is programmable between four to eight hours.

In Example 11, the subject matter of any one or more of Examples 7-10 optionally includes at least one of the one or more second ventricular heart rate statistics that may include a heart rate stability of the representative ventricular heart rates computed from the second plurality of heart rate analysis windows. The atrial tachyarrhythmia detector circuit may be configured to detect the AT event further in response to the heart rate stability exceeding a stability threshold.

In Example 12, the subject matter of Example 11 optionally includes the atrial tachyarrhythmia detector circuit that may be configured to generate the heart rate stability using a histogram of the representative ventricular heart rates computed from the second plurality of heart rate analysis windows.

In Example 13, the subject matter of any one or more of Examples 1-12 optionally includes a parameter adjuster circuit configured to reduce the specific duration in response to the detection of the AT event.

In Example 14, the subject matter of any one or more of Examples 1-13 optionally includes the atrial tachyarrhythmia detector circuit that may be configured to detect the AT event including: detect an atrial flutter (AFL) event in response to the one or more second ventricular heart rate statistics satisfying an AFL detection condition including a AFL heart rate threshold throughout an AFL duration; and detect a fast AFL event in response to the one or more second ventricular heart rate statistics satisfying a fast AFL detection condition including a fast AFL heart rate threshold throughout a fast AFL duration; wherein the fast AFL heart rate threshold is greater than the AFL heart rate threshold, and the fast AFL duration is shorter than the AFL duration.

In Example 15, the subject matter of any one or more of Examples 1-14 optionally includes an ambulatory device that includes at least a portion of the atrial tachyarrhythmia detector circuit.

Example 16 is a method for detecting atrial tachyarrhythmia using an arrhythmia detector system. The method comprises steps of, via the arrhythmia detector system, determining a plurality of representative ventricular heart rates within a first plurality of heart rate analysis windows, and generating a first ventricular heart rate statistic using the plurality of representative ventricular heart rates within the first plurality of heart rate analysis windows; determining a plurality of representative ventricular heart rates within a second plurality of heart rate analysis windows and generating one or more second ventricular heart rate statistics during a specific duration; detecting an atrial tachyarrhythmia (AT) event in response to the first ventricular heart rate statistic satisfying a first condition and the one or more second ventricular heart rate statistics satisfying a second condition throughout the specific duration; and outputting the detected AT to a user or a process.

In Example 17, the subject matter of Example 16 optionally includes determining the representative ventricular heart rates, each of which includes a central tendency indicating a most frequent heart rate among the plurality of heart rate measurements within a respective heart rate analysis window.

In Example 18, the subject matter of Example 16 optionally includes the first ventricular heart rate statistic that may include a first relative number of the representative ventricular heart rates, within the first plurality of heart rate analysis windows, that exceed a heart rate threshold.

In Example 19, the subject matter of Example 16 optionally includes the one or more second ventricular heart rate statistics that may include one or more of: a second relative number of the representative ventricular heart rates, within the second plurality of heart rate analysis windows, that exceed a heart rate threshold; or a heart rate stability of the representative ventricular heart rates computed from the second plurality of heart rate analysis windows.

In Example 20, the subject matter of Example 19 optionally includes detecting the AT event including detecting an atrial flutter (AFL) event. The heart rate threshold may be programmable between 100 and 150 beats per minute; and the specific duration is programmable between four to eight hours.

In Example 21, the subject matter of Example 16 optionally includes reducing the specific duration in response to the detection of the AT event.

Example 22 is a system for detecting atrial arrhythmias. The system comprises an atrial tachyarrhythmia detector circuit. The atrial tachyarrhythmia detector circuit may be configured to receive a plurality of representative ventricular heart rates; detect an atrial fibrillation (AF) event using at least a portion of the plurality of the representative ventricular heart rates over a first time period; and detect an atrial flutter (AFL) event using at least a portion of the plurality of the representative ventricular heart rates over a second time period. The first time period may be on the order of seconds or minutes. The second time period may be on the order of hours.

In Example 23, the subject matter of Example 22 optionally includes the atrial tachyarrhythmia detector circuit that may be configured to: generate a first ventricular heart rate statistic using the plurality of representative ventricular heart rates within a first plurality of heart rate analysis windows; generate one or more second ventricular heart rate statistics during an AF duration within the first time period, the one or more second ventricular heart rate statistics each generated using the plurality of representative ventricular heart rates within a second plurality of heart rate analysis windows; generate one or more third ventricular heart rate statistics during an AFL duration within the second time period, the one or more third ventricular heart rate statistics each generated using the plurality of representative ventricular heart rates within a third plurality of heart rate analysis windows; detect the AF event using the first ventricular heart rate statistic and the one or more second ventricular heart rate statistics generated during the AF duration; and detect the AFL event using the first ventricular heart rate statistic and the one or more third ventricular heart rate statistics generated during the AFL duration.

In Example 24, the subject matter of Example 22 optionally includes the atrial tachyarrhythmia detector circuit that may be configured to detect a fast AFL event using at least a portion of the plurality of the representative ventricular heart rates over a third time period. The third time period may be on the order of hours and shorter than the second time period.

The systems, devices, and methods discussed in this document may improve the medical technology of automated cardiac rhythm management (CRM) and prevention of worsening of cardiac function. The heart rate-based arrhythmia detection may also enhance the performance and functionality of an implantable CRM device, in certain examples, increasing the specificity of existing AF or AFL detection (e.g., reducing false positives), such that system performance can be improved with little to no additional cost, while reducing costs associated with false AF or AFL detection, or manual inspection required by such false determinations. In other examples, existing system performance can be maintained (e.g., high AF or AFL sensitivity and specificity, etc.) using lower cost or less obtrusive systems, apparatus, and methods. For example, because the system or device does not require direct atrial activity sensing for atrial tachyarrhythmias detection, the system complexity and implementation cost may be reduced. It may particularly be beneficial for patient not indicated for atrial lead implantation either for atrial activity sensing or for atrial pacing. The heart rate-based arrhythmia detection also allows for more efficient use of device memory, such as by storing ventricular heart rate statistics that are clinically relevant to arrhythmia recognition, and a smaller number of potential AF or AFL events. As fewer alarms are provided, battery life can be extended, fewer unnecessary drugs and procedures may be scheduled, prescribed, or provided, and an overall system cost savings may be realized.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for detecting cardiac arrhythmias such as an atrial tachyarrhythmia (AT). Representative ventricular heart rates may be detected from physiological signals within heart rate analysis windows. An atrial tachyarrhythmia detector circuit may generate first ventricular heart rate statistic from representative ventricular heart rates determined within a first plurality of heart rate analysis windows, and generate one or more second ventricular heart rate statistics from a plurality of representative ventricular heart rates determined within a second plurality of heart rate analysis windows during a specific duration. One or more types of sustained AT events may be detected in response to the second ventricular heart rate statistics satisfy a specific condition throughout the specific duration.

Figure 1:
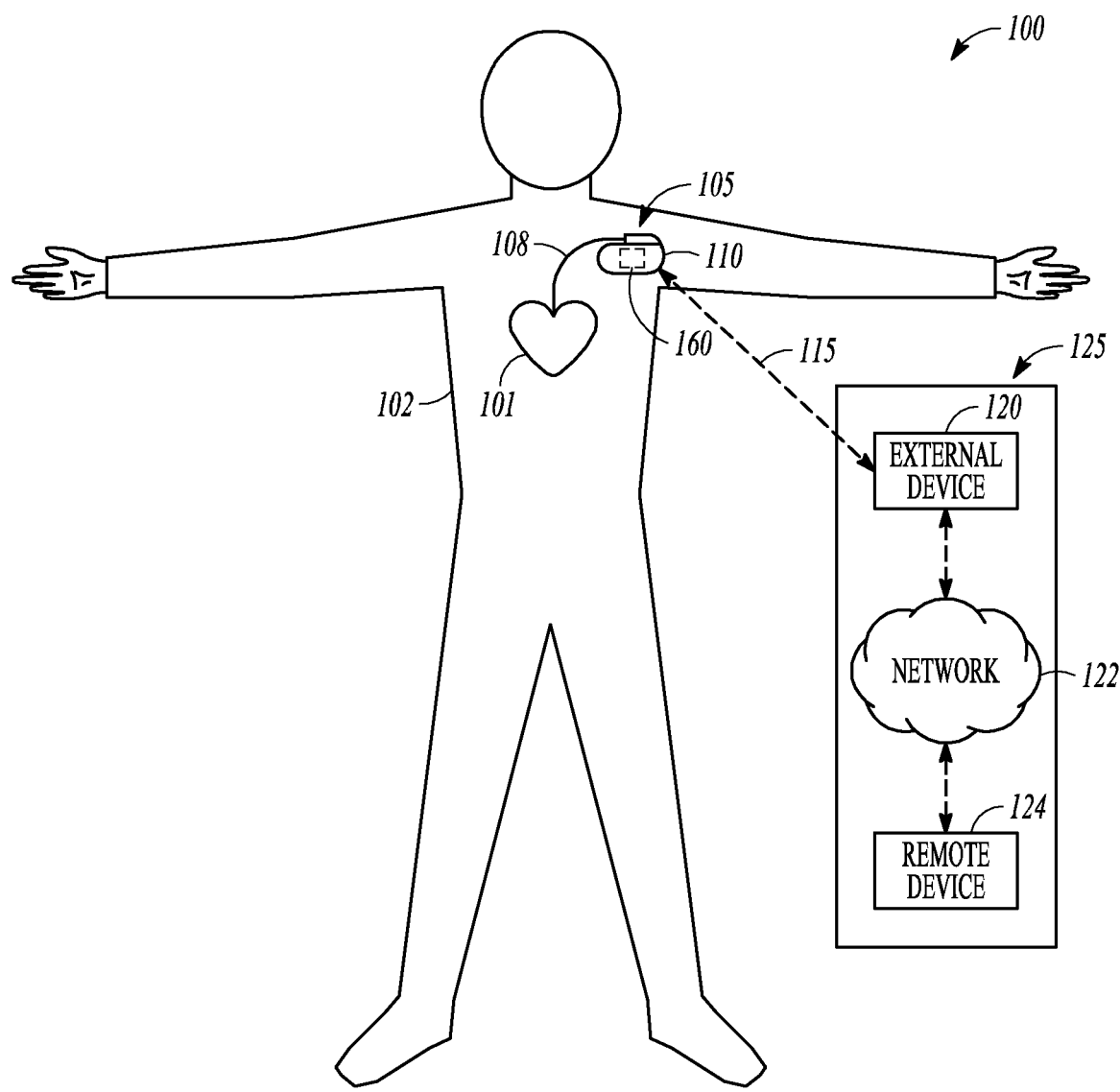
FIG. 1 illustrates an example of a Cardiac Rhythm Management (CRM) system and portions of an environment in which the CRM system may operate.

FIG. 1 illustrates generally an example of a Cardiac Rhythm Management (CRM) system 100 and portions of an environment in which the system 100 may operate. The CRM system 100 may include an ambulatory system 105 associated with a patient 102, an external system 125, and a telemetry link 115 providing for communication between the ambulatory system 105 and the external system 125.

The ambulatory system 105 may include an ambulatory medical device (AMD) 110. In an example, the AMD 110 may be an implantable device subcutaneously implanted in a chest, abdomen, or other parts of the patient 102. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 may alternatively or additionally include subcutaneously implanted devices, wearable medical devices, or other external monitoring or therapeutic medical devices or equipment.

The AMD 110 may be coupled to a lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined based on the patient need and the capability of the AMD 110. The associated electrodes on the lead system 108 may be positioned at the patient's thorax or abdomen to sense a physiological signal indicative of cardiac activity, or physiological responses to diagnostic or therapeutic stimulations to a target tissue. By way of example and not limitation, and as illustrated in FIG. 1, the lead system 108 may be configured to be surgically inserted into, or positioned on the surface of, a heart 101. The electrodes on the lead system 108 may be positioned on a portion of a heart 101, such as a right atrium (RA), a right ventricle (RV), a left atrium (LA), or a left ventricle (LV), or any tissue between or near the heart portions. In some examples, the lead system 108 and the associated electrodes may alternatively be positioned on other parts of the body to sense a physiological signal containing information about patient heart rate or pulse rate. In an example, the ambulatory system 105 may include one or more leadless sensors not being tethered to the AMD 110 via the lead system 108. The leadless ambulatory sensors may be configured to sense a physiological signal and wirelessly communicate with the AMD 110.

The AMD 110 may be configured as a monitoring and diagnostic device. The AMD 110 may include a hermetically sealed can that houses one or more of a sensing circuit, a control circuit, a communication circuit, and a battery, among other components. The sensing circuit may sense a physiological signal, such as by using a physiological sensor or the electrodes associated with the lead system 108. Examples of the physiological signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, RV pressure, LV coronary pressure, coronary blood temperature, blood oxygen saturation, one or more heart sounds, intracardiac acceleration, physical activity or exertion level, physiological response to activity, posture, respiration rate, tidal volume, respiratory sounds, body weight, or body temperature.

In an example, the AMD 110 may include a cardiac arrhythmia detection circuit 160 configured to detect an atrial tachyarrhythmia from the patient 102. The sensed physiological signal may contain information about patient heart rate or pulse rate. The cardiac arrhythmia detection circuit 160 may generate ventricular heart rate statistics from the sensed physiological signal. The ventricular heart rate statistics may indicate sustained excessive heart rate throughout a specific period of duration. The cardiac arrhythmia detection circuit 160 may detect an atrial tachyarrhythmia (AT) event, such as one or more of an atrial flutter (AFL) or an atrial fibrillation (AF) event, in response to the ventricular heart rate statistics satisfy specific conditions. The AMD 110 may output the detected AT event to a user such as the patient or a clinician, or to a process including, for example, an instance of a computer program executable in a microprocessor. In an example, the process may include an automated generation of recommendations for anti-arrhythmic therapy, or a recommendation for further diagnostic test or treatment.

The AMD 110 may alternatively be configured as a therapeutic device configured to treat arrhythmia or other heart conditions. The AMD 110 may additionally include a therapy unit that may generate and deliver one or more therapies. The therapy may be delivered to the patient 102 via the lead system 108 and the associated electrodes. The therapies may include electrical, magnetic, or other types of therapy. The therapy may include anti-arrhythmic therapy to treat an arrhythmia or to treat or control one or more complications from arrhythmias, such as syncope, congestive heart failure, or stroke, among others. Examples of the anti-arrhythmic therapy may include pacing, cardioversion, defibrillation, neuromodulation, drug therapies, or biological therapies, among other types of therapies. In an example, the therapies may include cardiac resynchronization therapy (CRT) for rectifying dyssynchrony and improving cardiac function in CHF patients. In some examples, the AMD 110 may include a drug delivery system such as a drug infusion pump to deliver drugs to the patient for managing arrhythmias or complications from arrhythmias.

Although the discussion herein with respect to the AMD 110 focuses on implantable system, this is meant only by way of example and not limitation. It is within the contemplation of the inventors and within the scope of this document, that the systems, devices, and methods discussed herein may also be implemented in, and executed by, a subcutaneous medical device such as a subcutaneous monitor or diagnostic device, wearable medical devices (e.g., watch-like devices, patch-based devices, or other accessories), or other ambulatory medical devices.

The external system 125 may be communicated with the AMD 110 via a communication link 115. The external system 125 may include a dedicated hardware/software system such as a programmer, a remote server-based patient management system, or alternatively a system defined predominantly by software running on a standard personal computer. The external system 125 may be used to control the operation of the AMD 110. The external system 125 may additionally receive via the communication link 115 information acquired by AMD 110, such as one or more physiological signals.

By way of example and not limitation, the external system 125 may include an external device 120 in proximity of the AMD 110, a remote device 124 in a location relatively distant from the AMD 110, and a telecommunication network 122 linking the external device 120 and the remote device 124. The telemetry link 115 may be an inductive telemetry link, a capacitive telemetry link, or a radio-frequency (RF) telemetry link. The telemetry link 115 may provide for data transmission from the AMD 110 to the external system 125. This may include, for example, transmitting real-time physiological data acquired by the AMD 110, extracting physiological data acquired by and stored in the AMD 110, extracting patient history data such as data indicative of occurrences of arrhythmias, occurrences of decompensation, and therapy deliveries recorded in the AMD 110, and extracting data indicating an operational status of the AMD 110 (e.g., battery status and lead impedance). The telemetry link 115 may also provide for data transmission from the external system 125 to the AMD 110. This may include, for example, programming the AMD 110 to perform one or more of acquiring physiological data, performing at least one self-diagnostic test (such as for a device operational status), analyzing the physiological data to detect cardiac arrhythmias, or optionally delivering or adjusting a therapy to the patient 102.

One or more of the external device 120 or the remote device 124 may include a display for displaying the physiological or functional signals, or alerts, alarms, emergency calls, or other forms of warnings to signal the detection of arrhythmias. In some examples, the external system 125 may include an external data processor configured to analyze the physiological or functional signals received by the AMD 110, and to confirm or reject the detection of arrhythmias. Computationally intensive algorithms, such as machine-learning algorithms, may be implemented in the external data processor to process the data retrospectively to detect cardia arrhythmias.

Portions of the AMD 110 or the external system 125 may be implemented using hardware, software, firmware, or combinations thereof. Portions of the AMD 110 or the external system 125 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
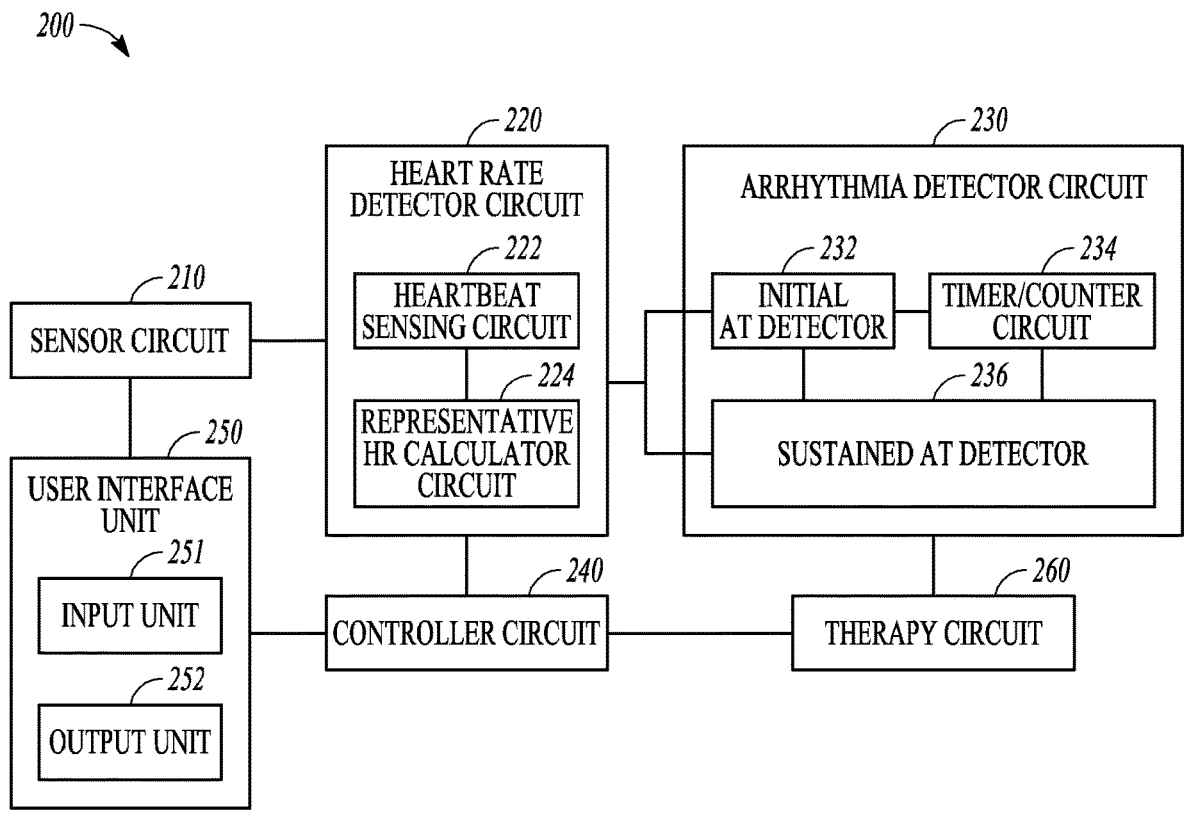
FIG. 2 illustrates generally an example of an arrhythmia detection system that may be configured to detect a cardiac arrhythmia from a patient, such as an AT event.

FIG. 2 illustrates generally an example of an arrhythmia detection system 200 that may be configured to detect atrial tachyarrhythmia from a patient, such as an AT event. Portions of the arrhythmia detection 200 may be included in the arrhythmia detection circuit 160 of the AMD 110. The arrhythmia detection system 200 may include one or more of a sensor circuit 210, a heart rate detector circuit 220, an arrhythmia detector circuit 230, a controller circuit 240, and a user interface unit 250. The arrhythmia detection system 200 may be configured as a cardiac monitor or diagnostic device for monitoring patient health status, or as a therapeutic device that additionally includes an optional therapy circuit 260.

The sensor circuit 210 may include a sense amplifier circuit to sense a physiological signal sensed from a patient via one or more implantable, wearable, or otherwise ambulatory sensors or electrodes associated with the patient. The sensed physiological signal may contain information about pulsatile cardiac activity, such as heart rate or pulse rate. Examples of the physiological signals may include surface electrocardiography (ECG) such as sensed from electrodes on the body surface, subcutaneous ECG such as sensed from electrodes placed under the skin, intracardiac electrogram (EGM) sensed from the one or more electrodes on the lead system 108, thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal such as sensed by an ambulatory accelerometer or acoustic sensors, physiological response to activity, apnea hypopnea index, one or more respiration signals such as a respiration rate signal or a tidal volume signal, brain natriuretic peptide (BNP), blood panel, sodium and potassium levels, glucose level and other biomarkers and bio-chemical markers, among others. The sensor circuit 210 may include one or more other sub-circuits to digitize, filter, or perform other signal conditioning operations on the received physiological signal.

In some examples, the physiological signals may be stored in a storage device such as an electronic medical record (EMR) system. The sensor circuit 210 may be configured to retrieve a physiological signal from the storage device in response to a command signal that is provided by a system user, or automatically generated in response to occurrence of a specific event.

The heart rate detector circuit 220 may be coupled to the sensor circuit 210 to detect representative ventricular heart rates. The heart rate detector circuit 220 may include a heartbeat sensing circuit 222 and a representative HR calculator circuit 224. The heartbeat sensing circuit 222 may be configured to sense heart beats from the sensed physiological signal. In an example, the sensor circuit 210 may sense a cardiac electrical signal such as an ECG, a subcutaneous ECG, or an intracardiac EGM, and the heartbeat sensing circuit 222 may detect from the cardiac electrical signal electrophysiological events indicative of cardiac depolarization or repolarization. Examples of the sensed electrophysiological events may include P wave, Q wave, R wave, QRS complex, or T wave in a surface or subcutaneous ECG or an intracardiac EGM. The sensor circuit 210 may additionally or alternatively include one or more sensors configured to sense cardiac mechanical activity indicative of heart contractions, and the heartbeat sensing circuit 222 may sense from the sensed cardiac mechanical activity mechano-physiological events indicative of one or more of atrial contraction, ventricular contraction, end of filling, end of emptying, or other specified phase during a cardiac contraction cycle. Examples of the sensors for sensing cardiac mechanical activity may include an accelerometer or a microphone configured to sense a heart sound signal or an endocardial acceleration signal from the heart, an impedance sensor configured to sense cyclic changes in cardiac impedance as a result of cardiac contractions, or a blood pressure sensor or a blood flow sensor for sensing pulsatile arterial pressure or flow as a result of cyclic cardiac contractions and opening/closure of heart valves, among other sensors. Examples of the mechano-physiological events may include: S1, S2, S3, or S4 heart sound from the sensed heart sound signal, peak or trough impedance from the cardiac impedance signal, or peak or trough blood pressure from the blood pressure signal, among others.

The representative HR calculator circuit 224 may be configured to determine a representative ventricular heart rate (rHR) using the sensed heartbeats within a heart rate analysis window. Heart rates, or cycle lengths (CLs), may be determined using the detected electrophysiological or mechano-physiological events. In an example, the CL may be measured a time interval (such as in a unit of second or millisecond) between two adjacent R waves (R-R interval) or P waves (P-P interval), or between adjacent impedance peaks or adjacent impedance troughs from the cardiac impedance signal, or an interval between two adjacent blood pressure peaks (i.e., systolic pressure) or adjacent blood pressure troughs (i.e., diastolic pressure) from the blood pressure signal, among others. The HR, in a unit of beat per minute (bpm), may be computed using the CL such as according to HR=60 seconds/CL.

The representative HR calculator circuit 224 may compute the rHR using a mean, a median, a mode, or other central tendency of a plurality of HR measurements within the heart rate analysis window. For example, a mode of the HR measurements may indicate most frequently occurring HR value in the plurality of HR measurements. The rHR may alternatively be computed as a specific percentile of the HR measurements, indicating a specific percentage (X %) of the HR measurements in a frequency distribution that are no greater than it. In an example, the frequency distribution includes a HR histogram computed from the HR measurements within the heart rate analysis window, and the X % is approximately between 25-75%. The size of the heart rate analysis window may be represented by a number of heartbeats or CLs, or a time period. In an example, the heart rate analysis window has a size of approximately 2-5 minutes. The heart rate analysis window may be programmable. A user may adjust the heart rate analysis window such as via the user interface unit 250.

Statistical measurement, such as the central tendency or percentile of HR distribution, may reduce the effects of noise, interference, oversensing, or undersensing on heartbeat sensing. It may also reduce the effect of intermittent conduction of the atrial impulses to the ventricle on HR detection. The rHR computed as such is a more robust estimate of the HR during atrial tachyarrhythmia.

The arrhythmia detector circuit 230 may be coupled to the representative HR calculator circuit 224 to detect an atrial tachyarrhythmia (AT) based on ventricular heart rate statistics determined from the representative HRs. Examples of AT may include atrial fibrillation (AF), atrial flutter (AFL), atrial tachycardia, paroxysmal supraventricular tachycardia (PSVT), Wolff-Parkinson-White (WPW) syndrome, among others. The arrhythmia detector circuit 230 may include an initial AT detector 232, a timer/counter circuit 234, and a sustained AT detector 236. The initial AT detector 232 is configured to generate a first ventricular heart rate statistic using a plurality of rHRs determined within a first plurality of heart rate analysis windows. The first ventricular heart rate statistic may include a first relative number, such as a fraction or a percentage, of the rHRs within the first plurality of heart rate analysis windows that exceed a heart rate threshold $HR_{T1}$. Such a first ventricular heart rate statistic may be denoted by "X out of Y" (X/Y) statistic, indicating that of Y representative ventricular heart rates $\{rHR_1, rHR_2, \ldots, rHR_Y\}$ computed from corresponding Y heart rate analysis windows, a total of X rHRs are "fast" heart rates that exceed the threshold $HR_{T1}$. The value of Y and $HR_{T1}$ may be pre-determined or user-programmable. In an example, Y may take a value between 10 and 20, and $HR_{T1}$ may take a value between 150 and 180 bpm.

The timer/counter circuit 234 may be preset or programmed to an AT duration $D_{AT}$, which may be represented by a specified number of heartbeats or CLs, or a specific period of time. The timer/counter circuit 234 may count time or detected heartbeats or CLs elapsed from the initial rate detection when the first ventricular heart rate statistic satisfies the first condition indicating an increase in heart rate. The first condition is also referred to hereinafter as an "entry condition," indicating a condition for entering sustained AT detection. In an example, the timer/counter circuit 234 may be initiated in response to at least eight of ten (8/10) rHRs are determined to be "fast" such as exceeding the heart rate threshold $HR_{T1}$. That is, the entry condition is X/Y≥8/10. Once initiated, the timer/counter circuit 234 may elapse or count down towards the end of $D_{AT}$. The timer/counter circuit 234 may get reset when the duration $D_{AT}$ expires and a sustained AT event is detected, or when an "exit condition" is satisfied prior to the expiration of $D_{AT}$ and no sustained AT event is detected.

The sustained AT detector 236, coupled to the initial AT detector 232 and the timer/counter circuit 234, may be configured to monitor the rHRs during the AT duration $D_{AT}$, and generate one or more second ventricular heart rate statistics. The one or more second ventricular heart rate statistics may each be generated from a plurality of representative ventricular heart rates (rHRs) determined within a second plurality of heart rate analysis windows. The second ventricular heart rate statistics may include a second relative number, such as a fraction or a percentage, of the rHRs within the second plurality of heart rate analysis windows that exceed a heart rate threshold $HR_{T2}$. The second ventricular heart rate statistics thus determined by be denoted as "M out of N" (M/N) statistic, indicating that among N representative ventricular heart rates $\{rHR_1, rHR_2, \ldots, rHR_N\}$ computed from corresponding N heart rate analysis windows, a total of M rHRs are "fast" heart rates that exceed the threshold $HR_{T2}$. The values of N and $HR_{T2}$ may each be pre-determined or user-programmable. In an example, N may take a value between 10 and 20, and $HR_{T2}$ may take a value between 100 and 160 bpm.

The detection parameters for initial rate detection (such as the Y and $HR_{T1}$) and the detection parameters for sustained AT detection (such as the N and $HR_{T2}$) may be independently programmed. In an example, the first and second ventricular heart rate statistics are computed from ten rHRs respectively computed from ten consecutive heart rate analysis windows, that is, Y=N=10. The heart rate thresholds $HR_{T2}$ may be identical to $HR_{T1}$. In a particular example, $HR_{T1}=HR_{T2}=150$ bpm. Alternatively, the $HR_{T2}$ and $HR_{T1}$ may be programmed to different values. In an example, $HR_{T1}=180$ bpm, and $HR_{T2}=150$ bpm.

The sustained AT detector 236 may be configured to detect the sustained AT episode in response to the one or more second ventricular heart rate statistics satisfying a second condition throughout the duration $D_{AT}$. In an example, the second ventricular heart rate statistic is "M out of N" (M/N) statistic as described above, and the second condition may be that at least six out of ten (6/10) rHRs, determined from any ten consecutive heart rate analysis windows throughout $D_{AT}$, exceed the heart rate threshold $HR_{T2}$, that is, M/N≥6/10. In an example, a moving set of ten consecutive heart rate analysis windows, hereinafter referred to as a "window set," may be examined throughout the duration $D_{AT}$. The resulting multiple window sets may be overlapped or non-overlapped to one another. The M/N statistic may be determined from each window set, and trended during the $D_{AT}$. A sustained AT episode is detected if the M/N statistics, corresponding to all the window sets during $D_{AT}$, satisfy the second condition of M/N≥6/10. If the M/N statistic corresponding to at least one window set during $D_{AT}$ fails to satisfy the second condition of M/N≥6/10, then no sustained AT is detected; and the timer/counter circuit 234 may reset the duration timer. Compared to X/Y≥8/10 which defines an "entry condition" that triggers the sustained AT detector 236 to begin a session of sustained AT detection, M/N<6/10 defines an "exit condition" that triggers the sustained AT detector 236 to exit the session of sustained AT detection. Examples of the moving window set for sustained AT detection is discussed below, such as with reference to FIG. 4.

In some examples, the second ventricular heart rate statistic may additionally or alternatively include a heart rate stability of the rHRs. The heart rate stability indicates a degree of variability or regularity of ventricular response to AT, and may be determined using the rHRs computed from the second plurality of heart rate analysis windows. Examples of the heart rate stability may include difference, variance, standard deviation, or other higher-order statistics that characterize the variability of the cycle length or heart rate. In an example, the heart rate stability may be computed using a histogram of the plurality of rHRs computed from the heart rate analysis windows. In another example, the heart rate stability may be derived from Lorenz plot (LP) of the rHRs. The LP is a scatterplot of the present HR or cycle length (CL) as a function of the preceding one or more CLs or HRs. The LP-based stability may include geometric indices generated from the LP of the CLs or HRs, such as maximal length of the LP shape, maximal width of the LP shape, a density or spreadness measure of the LP scatterplots, among others.

The heart rate stability may be trended during the AT duration $D_{AT}$. The heart rate stability may be computed from multiple window sets each consisting of N representative ventricular heart rates $\{rHR_1, rHR_2, \ldots, rHR_N\}$ used for computing the M/N statistics. The sustained AT detector 236 may be configured to detect the AT event using the trend of the heart rate stability, such as when the heart rate stability computed from all the window sets during $D_{AT}$ exceed a stability threshold or falls within a specified range. The sustained AT detector 236 may alternatively detect the AT event using both the M/N statistics and the heart rate stability measurements. In an example, an AT event is detected if (1) the M/N statistics corresponding to all the window sets during $D_{AT}$ satisfy M/N≥6/10 and (2) the heart rate stability computed from all the window sets during $D_{AT}$ exceed a stability threshold or falls within a specified range. If either the M/N statistic or the heart rate stability fails to satisfy their respective condition, then no sustained AT is detected; and the timer/counter circuit 234 may reset the duration timer.

One or more of the detection parameters, such as the heart rate threshold $HR_{T1}$ for initial rate detection, the heart rate threshold $HR_{T2}$ for sustained AT detection, the heart rate stability threshold, or the AT duration $D_{AT}$, among others, may be independently programmed according to the type of AT events to be detected. For example, AF may have distinct ventricular response pattern, including average heart rate and heart rate stability different from the heart rate and heart rate stability in a typical AFL. An AF or fast AFL with a faster and more irregular heart rate may reduce cardiac output and more significantly deteriorates patient hemodynamic stability, thus may require early detection and alert to the clinician for immediate treatment. On the contrary, AFL with slower and/or more regular heart rate may less likely cause substantial hemodynamic disturbance; and a longer monitoring session may be beneficial to avoid false positive detection of a non-AT event, such as a sinus rhythm or sinus tachycardia. As such, the duration for detecting an AFL event (denoted by $D_{AFL}$) can be substantially longer than the duration for detecting an AF event (denoted by $D_{AF}$). The time period for detecting AF, such as $D_{AF}$, may be on the order of seconds or minutes. The time period for detecting AFL, such as $D_{AFL}$, may be on the order of hours. In an example, by way of example and not limitation, the $D_{AFL}$ is programmable between 4-8 hours, and the DAF is programmable between 2-10 minutes.

The detection parameters may also be programmed in accordance with the degree of atrioventricular (AV) block during atrial tachyarrhythmias. For example, a 2:1 AV block may occur during AFL, resulting in a regular ventricular rate about half of the atrial rate. Other fixed ratios such as 3:1, 4:1, or 5:1 AV block may also be present. In addition to fixed ratio AV block, the AV block may also vary from beat to beat, causing an irregular ventricular rhythm. As such, the degree of AV block may affect ventricular response, including heart rate and heart rate stability. Heart rate and heart rate stability may also be different between typical (Type I) AFL and atypical (Type II) AFL. The detection parameters, such as the detection duration, may be programmed to different values to detect different types of AFL events.

In some examples, the arrhythmia detector circuit 230 may be configured to detect two or more types of AT events, such as AF, fast AFL, slow AFL, Type I AFL, Type II AFL, or atrial tachycardia, among others. The two or more types of AT events may be detected concurrently and independently in their respective detection zones. Each zone may be defined by a heart rate threshold or heart rate range. For example, a multi-zone AT detection may include a slow AFL zone may be defined by a heart rate range between 100-160 bpm, and a fast AFL (fAFL) zone may be defined by heart rate above 160 bpm. Alternatively, the zones may be defined by threshold or range of heart rate stability. Each zone may include respective detection criteria for detecting a specific type of AT event. Examples of programming a multi-zone AT detection for detecting two or more types of AT events are discussed below, such as with reference to FIG. 5.

As illustrated in FIG. 2, the heart rate detector circuit 220 or the arrhythmia detector circuit 230 may respectively include circuit sets comprising one or more other circuits or sub-circuits. The circuits or sub-circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

In various examples, the heart rate detector circuit 220 or the arrhythmia detector circuit 230 may be implemented as a part of a microprocessor circuit. The microprocessor circuit may be a dedicated processor such as a digital signal processor, application specific integrated circuit (ASIC), microprocessor, or other type of processor for processing information including the physiological signals received from the sensor circuit 210. Alternatively, the microprocessor circuit may be a general purpose processor that may receive and execute a set of instructions of performing the functions, methods, or techniques described herein.

The controller circuit 240 controls the operations of the sensor circuit 210, the heart rate detector circuit 220, the arrhythmia detector circuit 230, the user interface unit 250, and the data and instruction flow between these components. For example, the controller circuit 240 may control the determination of rHRs, initial rate detection, and sustained arrhythmia detection. The user interface unit 250 may include an input unit 251 and an output unit 252. In an example, at least a portion of the user interface unit 250 may be implemented in the external system 130. The input unit 251 may receive a user's programming input, such as parameters for initial and sustained arrhythmia detection, including the heart rate thresholds $HR_{T1}$ and $HR_{T2}$, the threshold for heart rate stability, and the AT duration $D_{AT}$, among others. In some examples, the input unit 251 may allow a user to program multiple detection zones, such as an AF zone, fast AFL (fAFL) zone, slow AFL zone, atrial tachycardia zone, etc. The input unit 251 may include an input device such as a keyboard, on-screen keyboard, mouse, trackball, touchpad, touch-screen, or other pointing or navigating devices. The input device may enable a system user to program the parameters used for sensing the physiological signals, detecting the arrhythmias, and generating alerts, among others.

The output unit 252 may generate a human-perceptible presentation of information including one or more of the detection of the atrial tachyarrhythmia. The output unit 252 may include a display for displaying the sensed physiological signal, intermediate measurements or computations such as the first and second ventricular heart rate statistics (e.g., the X/Y statistic, the M/N statistic, the trend of M/N statistic or the heart rate stability trend during the AT duration $D_{AT}$), types of AT detected (such as fast AT, slow AT, AF, or atrial tachycardia, among others), AT burden that indicates the time of sustained AT, among others. The output unit 252 may include a printer for printing hard copies of the detection information. The information may be presented in a table, a chart, a diagram, or any other types of textual, tabular, or graphical presentation formats. The presentation of the output information may include audio or other media format to alert the system user of the detected arrhythmic events. In an example, the output unit 252 may generate alerts, alarms, emergency calls, or other forms of warnings to signal the system user about the detected arrhythmic events.

The output unit 252 may output a programming recommendation for adjusting one or more arrhythmia detection parameters, such as the detection duration $D_{AT}$. In an example, the sustained AT detector 236 may use a detection duration $D_{AFL}$ of approximately 5-8 hours to detect a sustained AFL event. A typical AFL event may last for a substantially longer time than other confounding rhythms, such as a sinus rhythm with elevated heart rate (e.g., sinus tachycardia) during tolerable physical activities. The AFL event may sustain at least as long as, or even longer than, $D_{AFL}$, while the confounding high-rate sinus rhythm generally does not sustain throughout the duration $D_{AFL}$. Therefore, a longer initial detection duration $D_{AFL}$ may help decrease false alarm rate in AFL detection and thus achieve a higher detection specificity. A long duration $D_{AFL}$, however, may cause misdetections of some AFL events with a shorter duration (e.g., shorter than $D_{AFL}$), and potentially compromise the detection sensitivity to AFL detection. To alleviate this effect on the sensitivity, when the arrhythmia detector circuit 230 detects a sustained AT event upon expiration of the duration timer, the output unit 252 may produce and present to a user a recommendation to decrease the detection duration $D_{AFL}$, such as a recommendation to adjust the $D_{AFL}$ to a shorter duration, such as a value between 2-5 hours, or to decrease the $D_{AFL}$ by a specified amount. The output unit 252 may be configured to enable a system user, such as a clinician, to review and adjudicate the detected AFL event, and reprogram, or select from a predetermined list, a duration $D_{AFL}$, optionally along with one or more other parameters. A shorter duration $D_{AFL}$ may improve the AFL detection sensitivity and the estimate of atrial tachyarrhythmia burden (e.g., time spent in arrhythmia), and may maintain or not substantially comprise the detection specificity.

The optional therapy circuit 260 may be configured to deliver a therapy to the patient in response to the detection of the AT event. Examples of the therapy may include electrostimulation therapy delivered to the heart, a nerve tissue, other target tissues, a cardioversion therapy, a defibrillation therapy, or drug therapy including delivering drug to a tissue or organ. In some examples, the therapy circuit 260 may modify an existing therapy, such as adjust a stimulation parameter or drug dosage.

Figure 3:
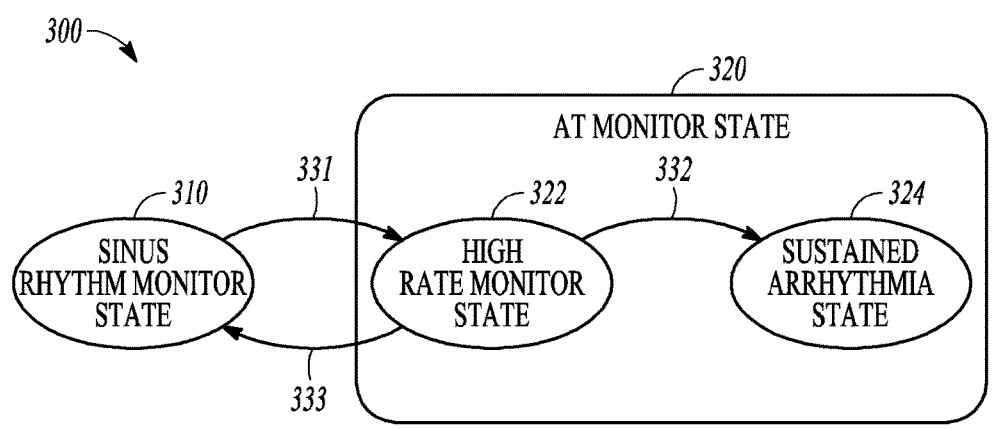
FIG. 3 illustrates generally a diagram of a state machine of operational states during arrhythmia detection and transitions among these states.

FIG. 3 illustrates generally a diagram of a state machine 300 of operational states during arrhythmia detection and transitions among these states. The state machine 300 may be implemented in and executed by portions of the system 200, such as the heart rate detector circuit 220 and the arrhythmia detector circuit 230. Alternatively, the state machine 300 may be implemented as computer programs stored in a memory, and executed by a microprocessor that processes the sensed physiological signal and generates output of arrhythmia detection. By way of example and not limitation, the state machine 300 may include a sinus rhythm monitor state 310, and an atrial tachyarrhythmia (AT) monitor state 320 that may include a high rate monitor state 322 and a sustained arrhythmia state 324.

The sinus rhythm monitor state 310 represents a state of cardiac monitoring at non-elevated heart rate, such as a state of normal sinus rhythm. Cardiac monitoring at state 310 may be performed via the sensor circuit 210 for sensing a physiological signal containing information about heart rate or pulse rate, and via the heart rate detector circuit 220 for sensing the representative ventricular heart rates (rHRs), and generating the first ventricular heart rate statistic such as the X/Y statistic. A transition 331 to the high rate monitor state 322 occurs when the first ventricular heart rate statistic satisfies a first condition indicating a heart rate elevation susceptive of tachyarrhythmia. In an example, the state transition 331 is triggered when the X/Y statistic satisfies an "entry condition" that indicates a substantial portion of the rHRs exceeding a heart rate threshold $HR_{T1}$, such as X/Y≥8/10.

The high rate monitor state 322 represents a state of cardiac monitoring at elevated heart rate. Cardiac monitoring at state 322 may be performed via the arrhythmia detector circuit 230, where the rHRs are monitored throughout a specific duration $D_{AT}$. One or more second ventricular heart rate statistics, such as one or more of the M/N statistics or heart rate stability measurements, may be generated and trended during the duration $D_{AT}$. A transition 332 to the sustained arrhythmia sate 324 occurs when the one or more second ventricular heart rate statistics satisfy respective second conditions throughout the duration $D_{AT}$. In an example, the state transition 332 is triggered when the M/N statistics, corresponding to all the window sets during the duration $D_{AT}$, satisfy M/N≥6/10 and that the heart rate stability measurements, computed from all the window sets during the duration $D_{AT}$, exceed a stability threshold or falls within a specific range. If at the high rate monitor state 322 one or more second ventricular heart rate statistics fail to satisfy their respective second conditions throughout the duration $D_{AT}$, then a transition 333 back to the sinus rhythm monitor state 310 occurs, and no sustained AT is deemed detected. In an example, the state transition 333 is triggered if the M/N statistic satisfies an "exit condition" that indicates an insufficient portion of the rHRs in a window set, prior to the expiration of $D_{AT}$, exceeding a heart rate threshold $HR_{T2}$, such as X/Y<6/10.

The sustained arrhythmia state 324 represents a state of sustained atrial tachyarrhythmia. The result of detection may be output to a user such as a clinician, or to a process such as an instance of a computer program executable in a microprocessor. In an example, the process may include computer-implemented generation of recommendations for anti-arrhythmic therapy, or a recommendation for further diagnostic test or treatment.

Figure 4:
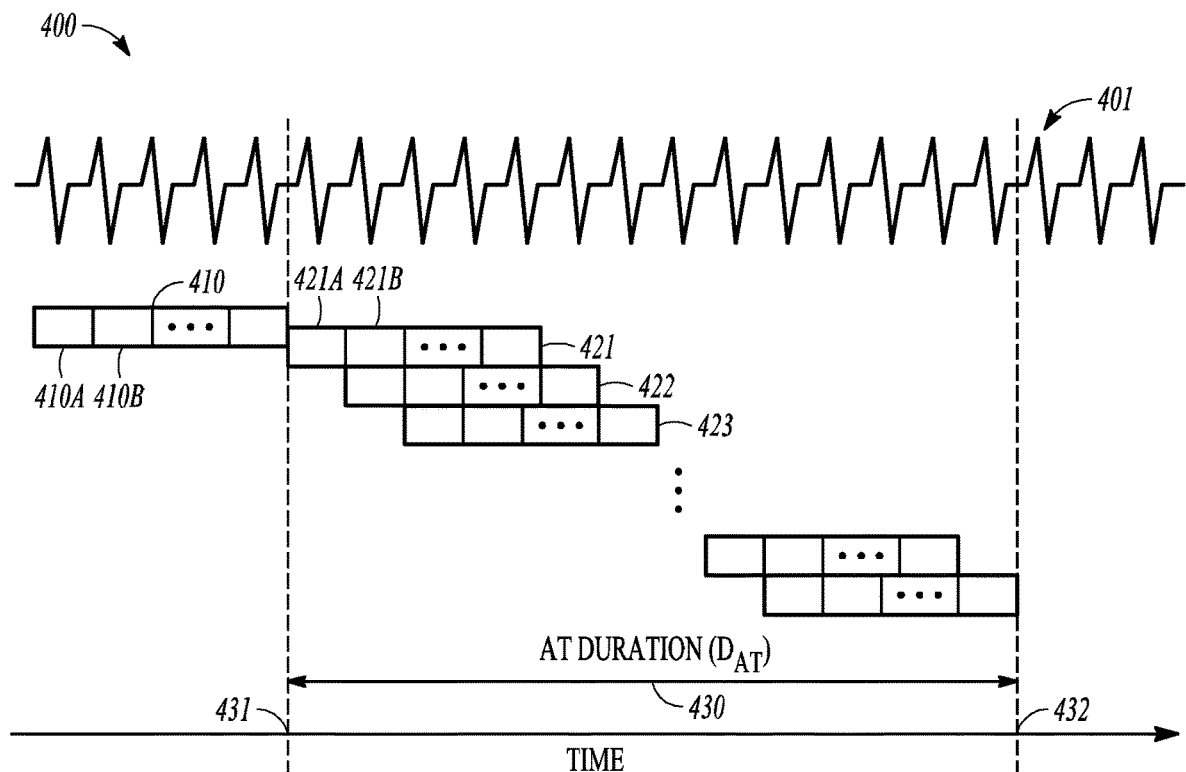
FIG. 4 illustrates a graph of an example of moving window sets for sustained AT detection.

FIG. 4 illustrates a graph 400 of an example of moving window sets for sustained AT detection. A physiological signal 401 may contain information about pulsatile cardiac electrical or mechanical activities. Heart rate may be detected via, for example, the heartbeat sensing circuit 222. A window set 410, consisting of a plurality of heart rate analysis windows 410A, 410B, . . . , may be applied to the physiological signal 401, and representative ventricular heart rates (rHRs) may be computed within each of heart rate analysis window. In an example, the window set 410 may consist of Y consecutive heart rate analysis windows. Each heart rate analysis window may have a specific size, represented by a specific number of heartbeats or CLs or a specific time period. In an example, the heart rate analysis window has a size of approximately 2-5 minutes. The rHRs may each be computed as a mode or another central tendency of the heart rate measurements within their respective heart rate analysis window. A first ventricular heart rate statistic, such as the X/Y statistic as previously discussed with reference to FIGS. 2-3, may be generated from the rHRs corresponding to the Y consecutive heart rate analysis windows in the window set 410.

When the X/Y statistic satisfies an "entry condition" indicating a substantial (e.g., 8/10) portion of the rHRs computed from the window set 410 exceed a heart rate threshold $HRT_1$, an initial rate detection is declared, and an AT duration timer may be initiated at time 431. The AT duration ($D_{AT}$) 430 may be programmed to specific value. A window set 421 may be established, consisting of a plurality of heart rate analysis windows 421A, 421B, . . . . Within each of the heart rate analysis windows, a respective representative ventricular heart rate rHR may be computed, such as using a mode or another central tendency of the heart rate measurements within the corresponding heart rate analysis window. A second ventricular heart rate statistic may be determined from the rHRs corresponding to the window set 421. In an example, the window set 421 may consist of N consecutive heart rate analysis windows, and the second ventricular heart rate statistic may include the M/N statistic or heart rate stability computed using the rHRs from the N consecutive heart rate analysis windows in the window set 421. When the second ventricular heart rate statistic satisfies a second condition, such as M/N≥6/10 and/or the heart rate stability exceed a stability threshold or falls within a specific range, the window set 421 may be shifted by a specific time or a specific number of heartbeats to form another window set 422. The window set 421 and 422 may be overlapped by a specific time period, a specific number of heartbeats, or a specific number of heart rate analysis window. In an example as illustrated in FIG. 4, the window set 421 may be shifted by one heart rate analysis window to form the window set 422. The second ventricular heart rate statistic may be similarly determined from the rHRs corresponding to N consecutive heart rate analysis windows in the window set 422. The moving window set may be established as such until it reaches the end of the duration $D_{AT}$ at 432. If the second ventricular heart rate statistics, computed from all the resultant window sets 421, 422, 423, . . . within the $D_{AT}$ satisfy the second condition, such as when (1) the M/N statistics corresponding to all the window sets during $D_{AT}$ satisfy M/N≥6/10 and (2) the heart rate stability computed from all the window sets during $D_{AT}$ exceed a stability threshold or falls within a specific range, then a sustained AT event may be detected at 432. However, if the second ventricular heart rate statistic corresponding to any one of the window sets 421, 422, 423, . . . fail to satisfy respective second conditions, such as when either the M/N statistic or the heart rate stability fails to satisfy their respective conditions, then no sustained AT is detected.

Figure 5:
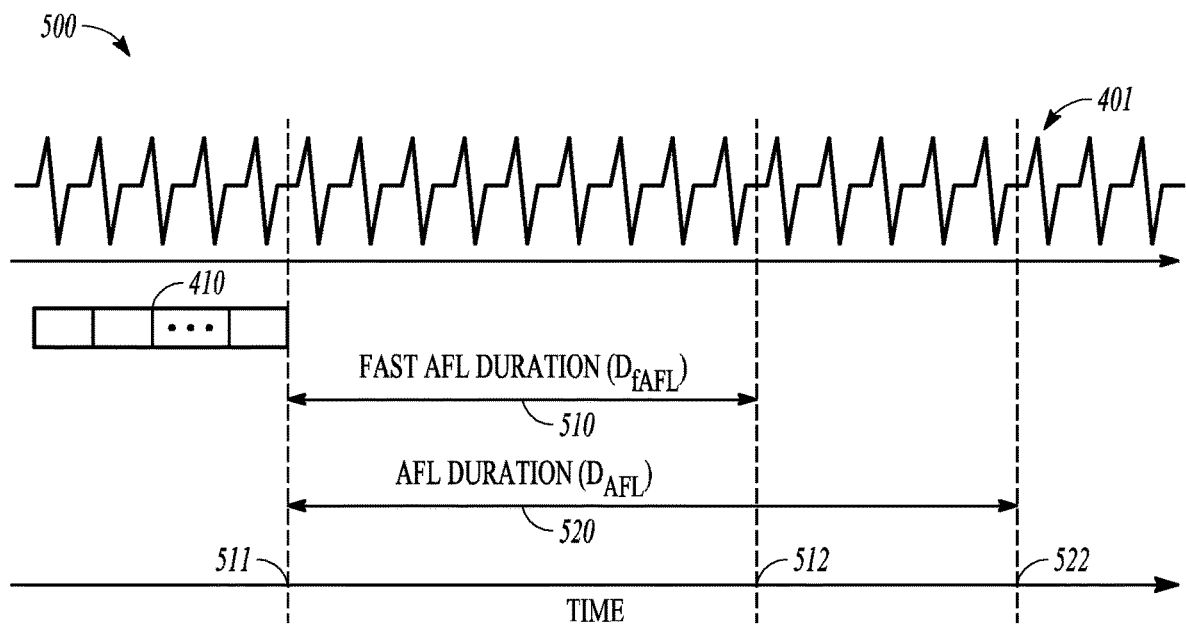
FIG. 5 illustrates a graph of an example of multi-zone atrial tachyarrhythmia detection.

FIG. 5 illustrates a graph 500 of an example of multi-zone atrial tachyarrhythmia detection. By way of example and not limitation, a two-zone detection is illustrated, including a fast AFL (fAFL) zone, and an AFL zone. Each zone defines criteria for detecting a specific type of AT event. In the example as illustrated in FIG. 5, arrhythmia detection in the AFL zone and the fAFL zone share initial rate detection using the window set 410, as discussed with reference to FIG. 4. When the first statistic indicates a substantial portion of the rHRs computed from the window set 410 exceed a heart rate threshold $HR_{T1}$, sustained rhythm detection at the AFL zone and the fAFL zone may be initiated at 511, and proceed concurrently and independently. In some examples (not shown), the initial rate detection in one zone (e.g., the fAFL zone) may be separate from and independent of the initial rate detection in another zone (e.g., the AFL zone). For example, each zone may involve an initial rate detection using a zone-specific window set 410, a zone-specific heart rate threshold $HR_{T1}$, or a zone-specific "entry condition."

Each of the multiple zones may define respective detection criteria for detecting a specific type of AT event. Detection parameters such as $HR_{T2}$ and the duration $D_{AT}$ may be independently programmed for each zone. The fAFL zone may have a higher programmed heart rate threshold ($HR_{fAFL}$) and a shorter duration 510 ($D_{fAFL}$) than the AFL zone, which has a lower heart rate threshold ($HR_{AFL}$) and longer duration 520 ($D_{AFL}$). In an example, the fAFL zone may be programmed to $HR_{fAFL}$=160 bpm and $D_{fAFL}$=2 hours, and the AFL zone may be programmed to $HR_{AFL}$=100 bpm and $D_{AFL}$=8 hours. The moving window sets as illustrated in FIG. 4 may be used for arrhythmia detection in each zone. In an example, one or more window sets, such as at one or more of the window sets within the $D_{AFL}$, may be used in both AFL detection and the fAFL detection. Representative ventricular heart rates generated from the heart rate analysis windows from each window set may be compared to the heart rate threshold $HR_{AFL}$ to determine the M/N statistic for the AFL zone ($M/N_{AFL}$). The same representative ventricular heart rates may be compared to the heart rate threshold $HR_{fAFL}$ to determine the M/N statistic for the fAFL zone ($M/N_{fAFL}$). Because the heart rate threshold $HR_{fAFL}$ is greater than the heart rate threshold $HR_{AFL}$, the $M/N_{fAFL}$ statistic that satisfies the condition $M/N_{fAFL} \geq 6/10$ in the fAFL zone may also satisfy the condition $M/N_{AFL} \geq 6/10$ in the AFL zone. As such, time spent in the higher-rate fAFL zone may count towards time in the lower-rate AFL zone. If the $M/N_{fAFL}$ statistic satisfies the specified condition (e.g., $M/N_{fAFL} \geq 6/10$) throughout the duration 510, then a fAFL event is detected at 512. The AFL duration timer has not expired at 512, and the detection of sustained arrhythmia in the AFL zone may continue beyond the time 512 up to the expiration of the AFL duration timer at 522. That is, the detection of fAFL would not automatically stop the ongoing detection at the lower-rate AFL zone. Alternatively, the detection at the AFL zone may terminate in response to the detection of fAFL at 512.

Additionally or alternatively, if the $M/N_{fAFL}$ statistic satisfies an "exit condition" such as $M/N_{fAFL} < 6/10$ prior to expiration of the fAFL duration timer at 512, the heart rate assessment and arrhythmia detection may continue in the lower-rate AFL zone up to the expiration of the AFL duration timer at 522. That is, the non-detection of fAFL would not automatically stop the ongoing detection at the lower-rate AFL zone. The detection or non-detection at each of the fAFL zone and the AFL zone may be independently output to a user or a process, such as via the output unit 252 such as to alert the user of the detection of AFL or fAFL. The detected AFL or fAFL episode may be forwarded to an external system such as a remote patient management system for further processing. In an example, the detected arrhythmia may be labeled as AFL, fAFL, or both AFL and fAFL, and presented in a display or in a hard copy of an arrhythmia report.

The multi-zone detection and detection report of each zone as discussed in this document may provide improved arrhythmia diagnostics including characterization of arrhythmia rate, arrhythmia burden, and the temporal profile of arrhythmia progression. In one example, a non-detection in the fAFL zone along with a detection in the AFL zone may indicate the arrhythmia rate, in average, may lie between $HR_{AFL}$ and $HR_{fAFL}$, the heart rate thresholds for the AFL zone and the fAFL zone. In another example, a detection in the fAFL zone along with a non-detection in the AFL zone may indicate that the AT episode starts with a higher rate at or above $HR_{fAFL}$ and sustains throughout the duration $D_{fAFL}$, and then slows down and finally drops below $HR_{AFL}$ at some point in time prior to the expiration of AFL duration timer at 522. The improved arrhythmia characterization may be used by the clinician to determine individualized diagnostic test and appropriate treatment regimens.

The multi-zone detection may additionally include a third AF zone. Detection of an AF event in the AF zone may include initial rate detection and the sustained AF detection using the moving window sets as illustrated in FIG. 4. Because the AF is typically accompanied by fast and irregular heart rate, which may compromise patient hemodynamic stability, the AF zone may be programmed with a duration $D_{AF}$ shorter than the AFL zone detection $D_{AFL}$. In an example, $D_{AF} = 2$ minutes. In some examples, an AF event may be detected based on heart rate stability, in lieu of or in addition to the heart rate such as the M/N statistic as previously discussed.

Figure 6:
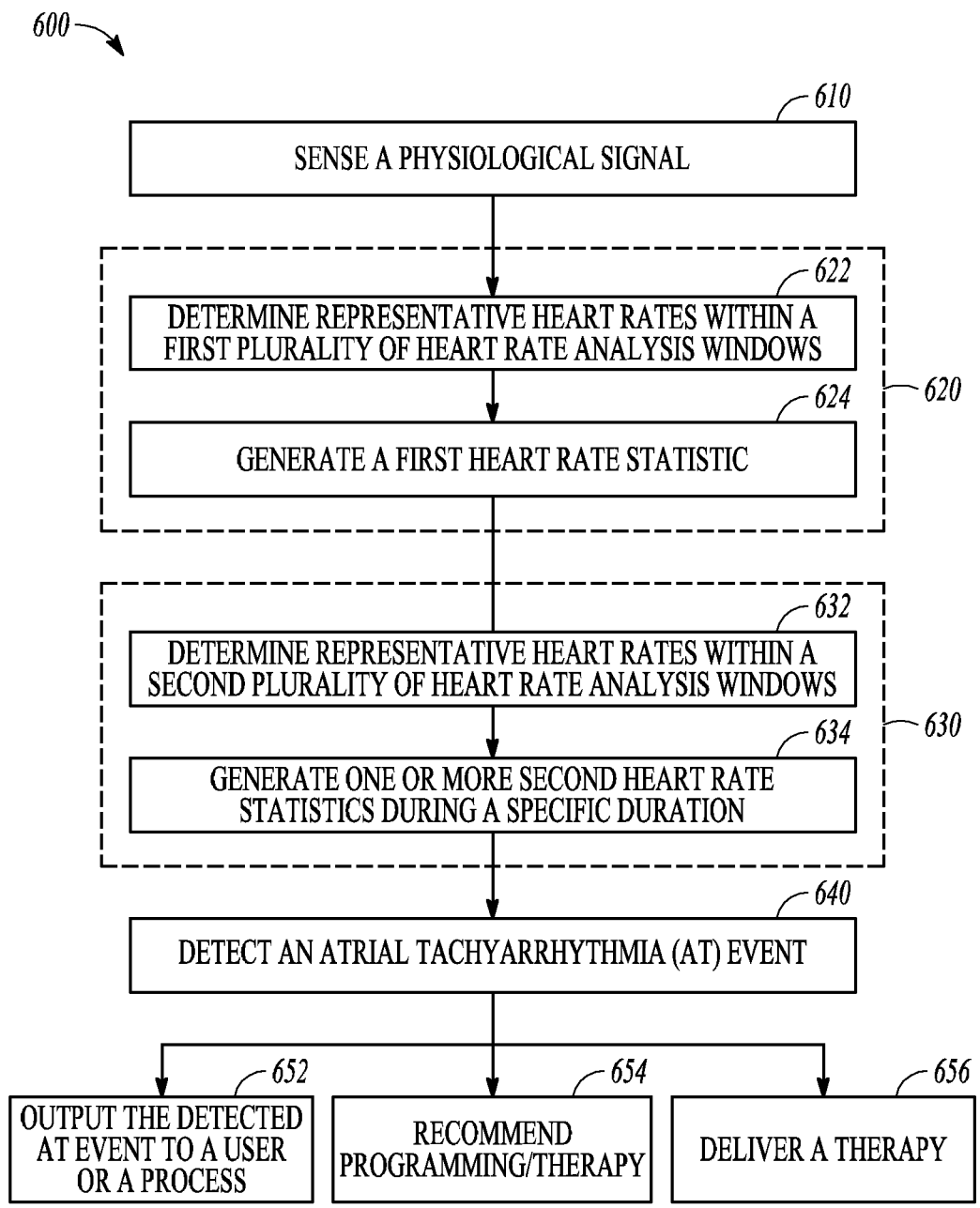
FIG. 6 illustrates generally an example of a method for detecting an cardiac arrhythmia from a patient.

FIG. 6 illustrates generally an example of a method 600 for detecting a cardiac arrhythmia from a patient. Examples of cardiac arrhythmias may include atrial fibrillation (AF), atrial flutter (AFL), atrial tachycardia, paroxysmal supraventricular tachycardia (PSVT), Wolff-Parkinson-White (WPW) syndrome, ventricular tachycardia, ventricular fibrillation, bradycardia, or sinus pauses, among others. The method 600 may be implemented and executed in an ambulatory medical device such as an implantable or wearable medical device, or in a remote patient management system. In an example, the method 600 may be implemented in and executed by the cardiac arrhythmia detection circuit 160 in the AMD 110, the external system 130, or the arrhythmia detection system 200.

The method 600 begins at 610, where a physiological signal may be sensed from a patient. The physiological signal may include a cardiac electrical signal such as an electrocardiography (ECG) or an intracardiac electrogram (EGM). The physiological signals may additionally or alternatively include signals indicative of cardiac mechanical activity, including thoracic or cardiac impedance signal, arterial pressure signal, pulmonary artery pressure signal, left atrial pressure signal, RV pressure signal, LV coronary pressure signal, heart sounds or endocardial acceleration signal, physiological response to activity, apnea hypopnea index, one or more respiration signals such as a respiration rate signal or a tidal volume signal, among others. The sensed physiological signal may be pre-processed, including one or more of signal amplification, digitization, filtering, or other signal conditioning operations. A plurality of electrophysiological or mechano-physiological events indicative of heart beats may be detected from the pre-processed physiological signal. In some examples, signal metrics such as timing parameters, or statistical or morphological parameters associated with the beats may be detected from the sensed physiological signal.

At 620, an initial rate detection of an arrhythmia may be executed, such as via the initial AT detector 232. Heart beats may be sensed from the sensed physiological signal, such as by measuring cardiac cycle length (CL) via the heartbeat sensing circuit 222. The heart rate (HR) may be computed from the measured CL. The initial AT detection at 620 may include determining representative ventricular heart rates (rHRs) within a first plurality of heart rate analysis windows of the sensed electrophysiological or mechano-physiological signal at 622. The rHRs may be computed as a mean, a median, a mode, or other central tendency of a plurality of HR measurements within the respective heart rate analysis window. In an example, the rHR corresponding to a heart rate analysis window may be computed as a mode of HR measurements, indicating the most frequently occurring HR value of the plurality of HR measurements. The rHR may alternatively be computed as a specific percentile of the HR measurements that indicates a percentage of the plurality of HR measurements in a frequency distribution (such as a HR histogram) that are no greater than that percentile. The heart rate analysis window may have a specific size, such as represented by a number of heartbeats or CLs or a time period. In an example, the heart rate analysis window is approximately 2-5 minutes. The heart rate analysis window may be programmable.

A first ventricular heart rate statistic may be generated at 624 using the plurality of rHRs determined within the first plurality of heart rate analysis windows. The first ventricular heart rate statistic may include a first relative number, such as a fraction or a percentage, of the rHRs within the first plurality of heart rate analysis windows that exceed a heart rate threshold $HR_{T1}$. In an example, the first ventricular heart rate statistic may include a "X out of Y" (X/Y) statistic, indicating of Y representative ventricular heart rates {$rHR_1$, $rHR_2$, ..., $rHR_Y$} computed from corresponding Y heart rate analysis windows, X rHRs are "fast" heart rates that exceed the threshold $HR_{T1}$. By way of example, Y may be a value between 10 and 20, and $HR_{T1}$ may take a value between 150 and 180 bpm.

Sustained AT detection may be initiated at 630 if the first ventricular heart rate statistic satisfies the first "entry condition" during the initial rate detection. The "entry condition" indicates criteria that have to be met to enter sustained AT detection process. In an example, the "entry condition" may include that at least eight of ten rHRs from the ten consecutive heart rate analysis windows exceed the heart rate threshold $HR_{T1}$. That is, X/Y≥8/10. The entry condition may also trigger a countdown or an elapse of a duration timer with a specific duration $D_{AT}$, such as via the timer/counter circuit 234.

The sustained AT detection at 630 may include determining rHRs within a second plurality of heart rate analysis windows at 632, and generating one or more second ventricular heart rate statistics from the plurality of rHRs at 634. In an example, the second ventricular heart rate statistics may include a second relative number, such as a fraction or a percentage, of the rHRs within the second plurality of heart rate analysis windows that exceed a heart rate threshold $HR_{T2}$. In an example, the second ventricular heart rate statistics may include an "M out of N" (M/N) statistic, indicating that among N representative ventricular heart rates {$rHR_1$, $rHR_2$, ..., $rHR_N$} computed from corresponding N heart rate analysis windows, M rHRs are "fast" heart rates that exceed the threshold $HR_{T2}$. Similar to the "X/Y" statistic during the initial rate detection, in "M/N" statistic the values of N and $HR_{T2}$ may be pre-determined or user-programmable. By way of example, N may be a value between 10-20, and $HR_{T2}$ may take a value between 100-160 bpm. The heart rate threshold $HR_{T2}$ for sustained AT detection may be identical to the heart rate threshold $HR_{T1}$ for initial rate detection. Alternatively, the $HR_{T2}$ and $HR_{T1}$ may be independently programmed to values different from each other. In an example, $HR_{T1}$=$HR_{T2}$=150 bpm. In another example, $HR_{T1}$=180 bpm, and $HR_{T2}$=150 bpm.

At 640, an AT event may be detected in response to the one or more second ventricular heart rate statistics satisfying a second condition throughout the duration $D_{AT}$. In an example, the second condition may be that at least six out of ten (6/10) rHRs, determined from any ten consecutive heart rate analysis windows throughout $D_{AT}$, exceed the heart rate threshold $HR_{T2}$. In an example, a moving window set of ten consecutive heart rate analysis windows may be examined throughout the duration $D_{AT}$. The window sets may be overlapped or non-overlapped to each other. The M/N statistic may be determined from each window set, and trended during the $D_{AT}$. A sustained AT episode is detected if the M/N statistics, corresponding to all the window sets during $D_{AT}$, satisfy the second condition of M/N≥6/10. If an M/N statistic corresponding to at least one window set during $D_{AT}$ fails to satisfy the second condition of M/N≥6/10, or an "exit condition" of M/N<6/10 is satisfied, then no sustained AT is detected, and the timer/counter circuit 234 may get reset.

In some examples, the second ventricular heart rate statistic at 634 may additionally or alternatively include a heart rate stability of the rHRs, such as computed from the second plurality of heart rate analysis windows. Examples of the heart rate stability may include difference, variance, standard deviation, or other higher-order statistics that indicate a degree of variability or regularity of the cycle length or the heart rate. The heart rate stability may be computed from multiple window sets each consisting of N representative ventricular heart rates {$rHR_1$, $rHR_2$, ..., $rHR_N$} used for computing the M/N statistics. The resulting heart rate stability measurements may be trended during $D_{AT}$. The sustained AT event may be detected at 640 using the trend of the heart rate stability, or using both the M/N statistics and the heart rate stability measurements. If either the M/N statistic or the heart rate stability fails to satisfy their respective conditions, then no sustained AT is detected.

The detected AT event may be used in one or more of the processes 652, 654, or 656. At 652, the AT event may be output to a user or a process, such as via the output unit 252 as illustrated in FIG. 2. In an example, information may be displayed on a display, including the sensed physiological signal, intermediate measurements or computations such as the first and second ventricular heart rate statistics, types of AT detected, or a AT burden indicating the time spent in a sustained AT, among others. Additionally or alternatively, a hard copy of the detection information may be generated.

At 654, a recommendation may be generate and provided to the user. The recommendation may include one or more of further diagnostic tests to be performed, anti-arrhythmic therapy for treat the detected arrhythmia or to alleviate the arrhythmic complications. The recommendation may include adjustment of one or more arrhythmia detection parameters, such as the detection duration $D_{AT}$. In an example, in detecting a typical AFL event, a duration $D_{AFL}$ of approximately 5-8 hours may initially be programmed. Such a long duration may help decrease the false alarm rate of AFL detection, and allow for a higher detection specificity. Upon the detection of sustained AT event, a recommendation of adjusting the duration $D_{AFL}$ may be presented to a user, such as to decrease the $D_{AFL}$ to a value between 2-5 hours. The system user, such as a clinician, may review and adjudicate the detected AFL event, and reprogram the duration $D_{AFL}$, optionally along with one or more other parameters, to improve the AFL detection sensitivity and the accuracy of atrial tachyarrhythmia burden estimate (e.g., time in arrhythmia), while maintaining or not substantially comprising the AFL detection specificity.

The method 600 may include the optional step 656 of delivering a therapy to the patient in response to the detection of the cardiac arrhythmia, such as via the optional therapy circuit 260 as illustrated in FIG. 2. Examples of the therapy may include electrostimulation therapy delivered to the heart, a nerve tissue, other target tissues, a cardioversion therapy, a defibrillation therapy, or drug therapy including delivering drug to a tissue or organ. In some examples, an existing therapy or treatment plan may be modified to treat the detected arrhythmia, such as modify patient follow-up schedule, or adjust a stimulation parameter or drug dosage.

Figure 7:
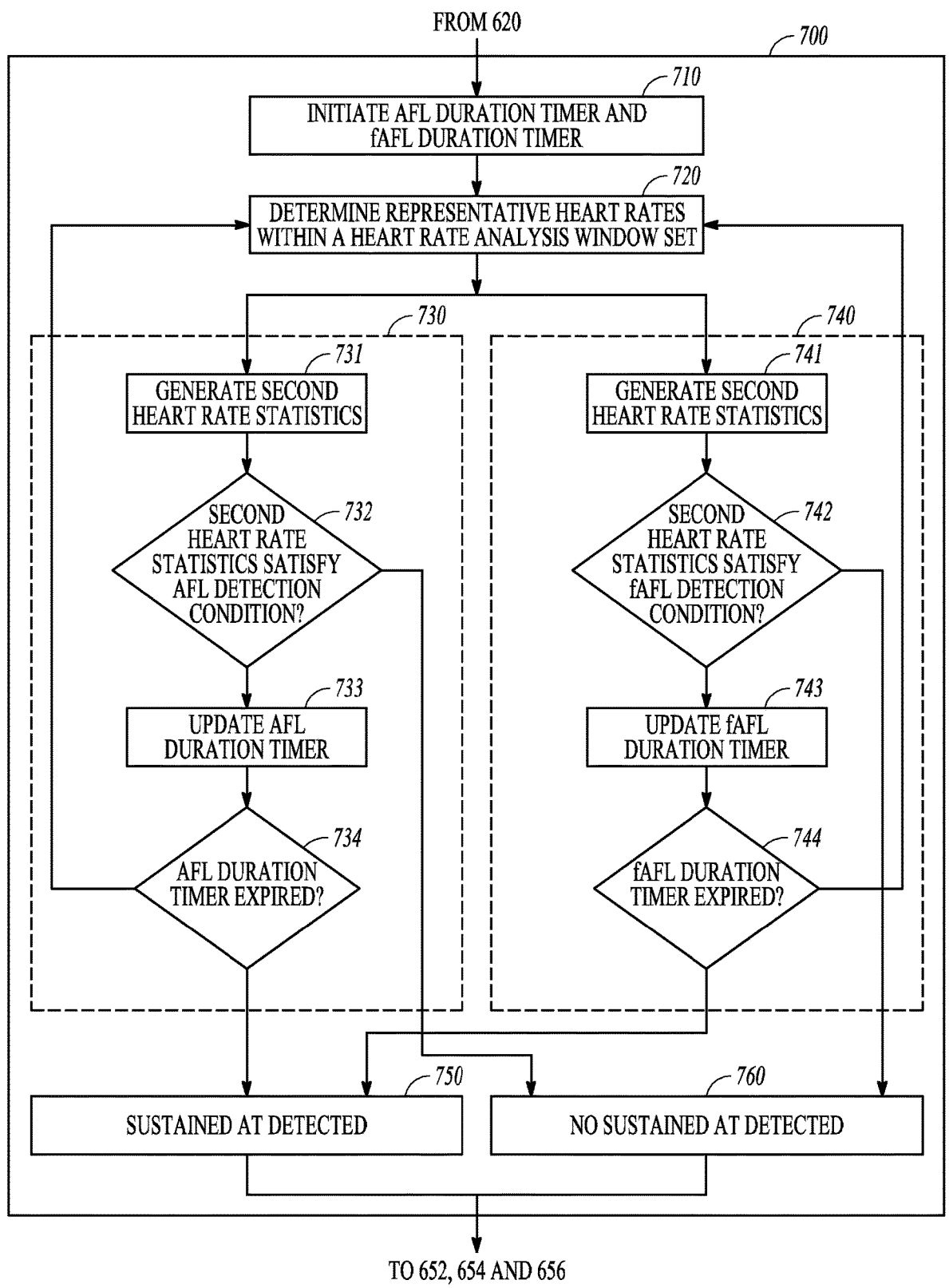
FIG. 7 illustrates generally an example of a method for a multi-zone detection of two or more atrial tachyarrhythmias.

FIG. 7 illustrates generally an example of a method 700 for a multi-zone detection of two or more atrial tachyarrhythmia, such as atrial fibrillation (AF), fast atrial flutter (AFL), slow AFL, Type I AFL, Type II AFL, or atrial tachycardia, among others. The method 700 may be an embodiment of at least a portion of the method 600, including steps 630 and 640. In an example, the method 700 may be implemented in and executed by the arrhythmia detection system 200 in FIG. 2.

By way of example and not limitation, the method 700 illustrates a two-zone AT detection, including detecting AFL event in an AFL zone and detecting fast AFL (fAFL) event in a fAFL zone. The AFL zone and the fAFL zone may share the initial rate detection 620, as discussed with reference to FIG. 6. When the first ventricular heart rate statistic indicates a substantial portion of the rHRs computed from the window set 410 exceed a heart rate threshold $HRT_1$, sustained rhythm detection at the AFL zone and the fAFL zone may proceed concurrently and independently. Alternatively, the AFL zone and the fAFL zone detection may include separate and independent initial rate detections with their respective "entry conditions."

At 710, an AFL duration timer and a fAFL duration timer may be initiated in response to the first ventricular heart rate statistic satisfies the first condition, such as at least eight of ten consecutive rHRs exceed the heart rate threshold $HR_{T1}$. The fAFL zone may have a duration shorter than the AFL zone. In an example, the duration for the fAFL zone is $D_{fAFL}=2$ hours, and the duration for the AFL zone is $D_{AFL}=8$ hours.

At 720, representative ventricular heart rates (rHRs) may be determined within a heart rate analysis window set, such as a set of N consecutive heart rate analysis windows. In an example, N=10. The rHRs generated from the heart rate analysis window set may be used by both the AFL zone detection 730 and the fAFL zone detection 740. The AFL zone detection 730 and the fAFL zone detection 740 may proceed concurrently and independently. Each zone defines respective detection criteria for detecting the specified type of AT event, including one or more second ventricular heart rate statistics and the heart rate threshold $HR_{T2}$.

At 731, second ventricular heart rate statistics, such as an M/N statistic, may be generated by comparing the plurality of rHRs generated at 720 to a heart rate threshold of the AFL zone ($HR_{AFL}$). In an example, $HR_{AFL}=100$ bpm. At 732, the second ventricular heart rate statistics may be compared against the specific second condition. If the second ventricular heart rate statistics satisfies the AFL detection condition, such as at least six out of ten (6/10) rHRs generated at 720 from ten consecutive heart rate analysis windows exceed $HR_{AFL}$, then at 733 the AFL duration timer may be updated. In an example, update of the AFL duration timer may be achieved via moving window sets as illustrated in FIG. 5. A shift of a window set to the right along the time axis corresponds to an elapse of time or countdown of the duration $D_{AFL}$. At 734, the AFL duration timer is checked for expiration. If the AFL duration timer has not expired, arrhythmia detection in the AFL zone may continue at 720, where rHRs may be generated from a new heart rate analysis window set, and the second ventricular heart rate statistics (e.g., the M/N statistic) may be evaluated from the new time-shifted window set. If at 734 the AFL duration timer has expired, then the AFL is deemed sustained throughout the duration $D_{AFL}$; and a sustained AFL may be detected at 750. If at any time during $D_{AFL}$, the second ventricular heart rate statistics fail to satisfy the AFL detection condition at 732, then an "exit condition" is deemed satisfied; and a decision of no sustained AFL detection is made at 760.

The fAFL detection 740 may proceed concurrently with the AFL zone detection 730. The fAFL detection 740 may include steps similar to the AFL detection 730. At 741, the same plurality of rHRs generated at 720 may be compared to a heart rate threshold of the fAFL zone ($HR_{fAFL}$) to determine the second ventricular heart rate statistic. In an example, the heart rate threshold $HR_{fAFL}=160$ bpm. If the second ventricular heart rate statistics satisfy the fAFL detection condition, such as when at least six out of ten (6/10) rHRs exceed $HR_{fAFL}$, then at 743 the AFL duration timer may be updated. The fAFL duration timer is then checked for expiration at 744. If the fAFL duration timer has not expired, arrhythmia detection in the fAFL zone may continue at 720, where rHRs from a new heart rate analysis window set may be determined, and the second ventricular heart rate statistics (e.g., M/N statistic) may be evaluated from the new time-shifted window set. If at 744 the fAFL duration timer has expired, then the fAFL is deemed sustained throughout the duration $D_{fAFL}$; and a sustained fAFL is detected at 750. If at any time during the duration $D_{fAFL}$, the second ventricular heart rate statistic fail to satisfy the fAFL detection condition at 742, then an "exit condition" is deemed satisfied; and a decision of no detection of sustained fAFL is made at 760. The decisions of detection or no detection of AFL or fAFL may then be used by one or more of the processes 652, 654, or 656 as illustrated in FIG. 6.

Figure 8:
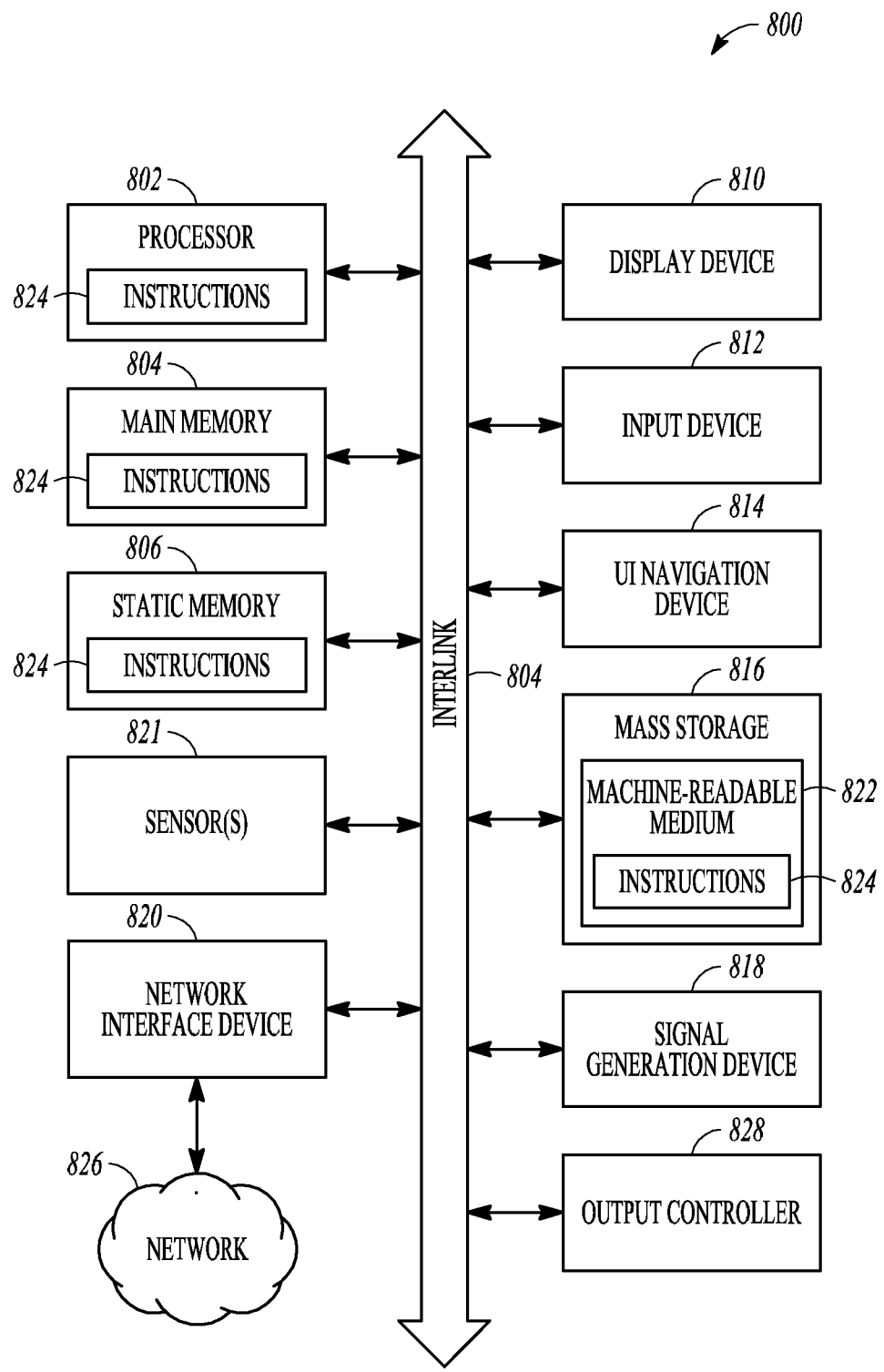
FIG. 8 illustrates generally a block diagram of an example machine upon which any one or more of the techniques (e.g., methodologies) discussed herein may perform.

FIG. 8 illustrates generally a block diagram of an example machine 800 upon which any one or more of the techniques (e.g., methodologies) discussed herein may perform. Portions of this description may apply to the computing framework of various portions of the LCP device, the IMD, or the external programmer.

In alternative embodiments, the machine 800 may operate as a standalone device or may be connected (e.g., networked) to other machines. In a networked deployment, the machine 800 may operate in the capacity of a server machine, a client machine, or both in server-client network environments. In an example, the machine 800 may act as a peer machine in peer-to-peer (P2P) (or other distributed) network environment. The machine 800 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 800 may include a hardware processor 802 (e.g., a central processing unit (CPU), a graphics processing unit (GPU), a hardware processor core, or any combination thereof), a main memory 804 and a static memory 806, some or all of which may communicate with each other via an interlink (e.g., bus) 808. The machine 800 may further include a display unit 810 (e.g., a raster display, vector display, holographic display, etc.), an alphanumeric input device 812 (e.g., a keyboard), and a user interface (UI) navigation device 814 (e.g., a mouse). In an example, the display unit 810, input device 812 and UI navigation device 814 may be a touch screen display. The machine 800 may additionally include a storage device (e.g., drive unit) 816, a signal generation device 818 (e.g., a speaker), a network interface device 820, and one or more sensors 821, such as a global positioning system (GPS) sensor, compass, accelerometer, or other sensor. The machine 800 may include an output controller 828, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 816 may include a machine readable medium 822 on which is stored one or more sets of data structures or instructions 824 (e.g., software) embodying or utilized by any one or more of the techniques or functions described herein. The instructions 824 may also reside, completely or at least partially, within the main memory 804, within static memory 806, or within the hardware processor 802 during execution thereof by the machine 800. In an example, one or any combination of the hardware processor 802, the main memory 804, the static memory 806, or the storage device 816 may constitute machine-readable media.

While the machine-readable medium 822 is illustrated as a single medium, the term "machine readable medium" may include a single medium or multiple media (e.g., a centralized or distributed database, and/or associated caches and servers) configured to store the one or more instructions 824.

The term "machine readable medium" may include any medium that is capable of storing, encoding, or carrying instructions for execution by the machine 800 and that cause the machine 800 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 824 may further be transmitted or received over a communications network 826 using a transmission medium via the network interface device 820 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 820 may include one or more physical jacks (e.g., Ethernet, coaxial, or phone jacks) or one or more antennas to connect to the communications network 826. In an example, the network interface device 820 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 800, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system for detecting atrial tachyarrhythmias, comprising:
an atrial tachyarrhythmia detector circuit configured to:
generate a first ventricular heart rate statistic using a plurality of representative ventricular heart rates determined within a first plurality of heart rate analysis windows;
generate one or more second ventricular heart rate statistics during a specific duration, the one or more second ventricular heart rate statistics each generated from a plurality of representative ventricular heart rates determined within a second plurality of heart rate analysis windows; and
detect an atrial tachyarrhythmia (AT) event including a sustained atrial flutter (AFL) event that sustains for the specific duration in response to: (1) the first ventricular heart rate statistic satisfying a first condition; and (2) the one or more second ventricular heart rate statistics satisfying a second condition throughout the specific duration.

2. The system of claim 1, comprising a therapy circuit configured to generate and deliver a cardiac therapy or a neural therapy in response to the detection of the sustained AFL event.

3. The system of claim 1, wherein each of the plurality of representative ventricular heart rates includes a central tendency indicating a most frequent heart rate among ventricular heart rate measurements within a respective heart rate analysis window.

4. The system of claim 1, wherein the first ventricular heart rate statistic includes a first relative number of the representative ventricular heart rates, within the first plurality of heart rate analysis windows, that exceed a heart rate threshold.

5. The system of claim 4, wherein the atrial tachyarrhythmia detector circuit is configured to generate one or more second ventricular heart rate statistics in response to the first ventricular heart rate statistic satisfying the first condition indicating that at least eight out of ten representative ventricular heart rates, determined from ten consecutive heart rate analysis windows, exceed the heart rate threshold.

6. The system of claim 1, wherein the one or more second ventricular heart rate statistics include a second relative number of the representative ventricular heart rates, within the second plurality of heart rate analysis windows, that exceed a heart rate threshold.

7. The system of claim 6, wherein the atrial tachyarrhythmia detector circuit is configured to detect the sustained AFL event in response to the one or more second ventricular heart rate statistics satisfying the second condition indicating that at least six out of ten representative ventricular heart rates, determined from any ten consecutive heart rate analysis windows throughout the specific duration, exceed the heart rate threshold.

8. The system of claim 6, wherein at least one of the one or more second ventricular heart rate statistics further includes a heart rate stability of the representative ventricular heart rates computed from the second plurality of heart rate analysis windows, and wherein the atrial tachyarrhythmia detector circuit is configured to detect the sustained AFL event further in response to the heart rate stability exceeding a stability threshold.

9. The system of claim 1, further comprising a parameter adjuster circuit configured to reduce the specific duration in response to the detection of the sustained AFL event.

10. The system of claim 1, wherein the atrial tachyarrhythmia detector circuit is configured to:
detect the sustained AFL event in response to the one or more second ventricular heart rate statistics satisfying an AFL detection condition including a AFL heart rate threshold throughout an AFL duration; and
detect a sustained fast AFL event in response to the one or more second ventricular heart rate statistics satisfying a fast AFL detection condition including a fast AFL heart rate threshold throughout a fast AFL duration;
wherein the fast AFL heart rate threshold is greater than the AFL heart rate threshold, and the fast AFL duration is shorter than the AFL duration.

11. The system of claim 1, wherein atrial tachyarrhythmia detector circuit is configured to detect the sustained AFL event that sustains for the specific duration in response to: (1) the first ventricular heart rate statistic satisfying a first condition; and (2) the one or more second ventricular heart rate statistics satisfying a second condition throughout the specific duration,
wherein the first ventricular heart rate statistic includes a first relative number of the representative ventricular heart rates, within the first plurality of heart rate analysis windows, that exceed a heart rate threshold, and wherein the first condition includes that a first number (X) out of a second number (Y) of representative ventricular heart rates, determined from consecutive heart rate analysis windows, exceed the heart rate threshold,
wherein the one or more second ventricular heart rate statistics include a second relative number of the representative ventricular heart rates, within the second plurality of heart rate analysis windows, that exceed a heart rate threshold, and wherein the second condition includes that a third number (M) out of a fourth number (N) of representative ventricular heart rates, determined from consecutive heart rate analysis windows throughout the specific duration, exceed the heart rate threshold,
wherein a ratio of X/Y is greater than a ratio of M/N.

12. A method for detecting atrial tachyarrhythmia using an arrhythmia detector system, the method comprising, via the arrhythmia detector system:
determining a plurality of representative ventricular heart rates within a first plurality of heart rate analysis windows, and generating a first ventricular heart rate statistic using the plurality of representative ventricular heart rates within the first plurality of heart rate analysis windows;
determining a plurality of representative ventricular heart rates within a second plurality of heart rate analysis windows and generating one or more second ventricular heart rate statistics during a specific duration;
detecting an atrial tachyarrhythmia (AT) event including a sustained atrial flutter (AFL) event that sustains for the specific duration in response to: (1) the first ventricular heart rate statistic satisfying a first condition; and (2) the one or more second ventricular heart rate statistics satisfying a second condition throughout the specific duration; and
outputting an indication of the detected AT event to a user or a process.

13. The method of claim 12, wherein each of the plurality of representative ventricular heart rates includes a central tendency indicating a most frequent heart rate among ventricular heart rate measurements within a respective heart rate analysis window.

14. The method of claim 12, wherein the first ventricular heart rate statistic includes a first relative number of the representative ventricular heart rates, within the first plurality of heart rate analysis windows, that exceed a heart rate threshold.

15. The method of claim 12, wherein the one or more second ventricular heart rate statistics include one or more of:
a second relative number of the representative ventricular heart rates, within the second plurality of heart rate analysis windows, that exceed a heart rate threshold; or
a heart rate stability of the representative ventricular heart rates computed from the second plurality of heart rate analysis windows.

16. The method of claim 15, wherein:
the heart rate threshold is programmable between 100 and 150 beats per minute; and
the specific duration is programmable between four to eight hours.

17. The method of claim 12, further comprising reducing the specific duration in response to the detection of the sustained AFL event.

18. A system for detecting atrial tachyarrhythmias, comprising:
an atrial tachyarrhythmia detector circuit configured to:
receive a plurality of representative ventricular heart rates; and
detect a sustained atrial flutter (AFL) event that sustains for a first time period in response to at least a portion of the plurality of the representative ventricular heart rates over the first time period satisfying a condition throughout the first time period, the first time period is on the order of hours.

19. The system of claim 18, wherein the atrial tachyarrhythmia detector circuit is configured to:
generate a first ventricular heart rate statistic using the plurality of representative ventricular heart rates within a first plurality of heart rate analysis windows; generate one or more second ventricular heart rate statistics during an AFL duration within the first time period, the one or more second ventricular heart rate statistics each generated using the plurality of representative ventricular heart rates within a second plurality of heart rate analysis windows;
and
detect the AFL event using the first ventricular heart rate statistic and the one or more second ventricular heart rate statistics generated during the AFL duration.

20. The system of claim 18, wherein the atrial tachyarrhythmia detector circuit is configured to detect a fast AFL event in response to at least a portion of the plurality of the representative ventricular heart rates over a second time period satisfying a condition throughout the second time period, wherein the second time period is on the order of hours and shorter than the first time period.

* * * * *